US010975204B2

(12) United States Patent
Willard et al.

(10) Patent No.: US 10,975,204 B2
(45) Date of Patent: Apr. 13, 2021

(54) SKIN-CONTACT PRODUCT HAVING MOISTURE AND MICROCLIMATE CONTROL

(71) Applicants: Nicolaas Petrus Willard, Valkenswaard (NL); Mareike Klee, Straelen (DE); Lucas Johannes Anna Maria Beckers, Veldhoven (NL); Dirk Burdinski, Essen (DE); Joyce Van Zanten, Waalre (NL); Willem Franke Pasveer, Dordrecht (NL); Biju Kumar Sreedharan Nair, Vendhoven (NL); David W. Smith, Oakmont, PA (US); Cornelis Petrus Hendriks, Eindhoven (NL)

(72) Inventors: Nicolaas Petrus Willard, Valkenswaard (NL); Mareike Klee, Straelen (DE); Lucas Johannes Anna Maria Beckers, Veldhoven (NL); Dirk Burdinski, Essen (DE); Joyce Van Zanten, Waalre (NL); Willem Franke Pasveer, Dordrecht (NL); Biju Kumar Sreedharan Nair, Vendhoven (NL); David W. Smith, Oakmont, PA (US); Cornelis Petrus Hendriks, Eindhoven (NL)

(73) Assignee: Koninklijke Philips N.V.

( * ) Notice: Subject to any disclaimer, the term of this patent is extended or adjusted under 35 U.S.C. 154(b) by 1067 days.

(21) Appl. No.: 15/447,198

(22) Filed: Mar. 2, 2017

(65) Prior Publication Data
US 2017/0240709 A1  Aug. 24, 2017

Related U.S. Application Data

(63) Continuation of application No. 14/127,538, filed as application No. PCT/IB2012/053201 on Jun. 25, 2012, now abandoned.

(60) Provisional application No. 61/586,876, filed on Jan. 16, 2012, provisional application No. 61/502,961, filed on Jun. 30, 2011.

(51) Int. Cl.
*C08L 41/00* (2006.01)
*C08G 77/28* (2006.01)
*A61M 16/06* (2006.01)
*A61M 16/00* (2006.01)
*A61M 16/08* (2006.01)
*C08G 77/08* (2006.01)
*C08J 9/00* (2006.01)
*C08L 43/04* (2006.01)

(52) U.S. Cl.
CPC ......... *C08G 77/28* (2013.01); *A61M 16/0057* (2013.01); *A61M 16/06* (2013.01); *A61M 16/0605* (2014.02); *A61M 16/0633* (2014.02); *A61M 16/0683* (2013.01); *A61M 16/0816* (2013.01); *C08G 77/08* (2013.01); *C08J 9/00* (2013.01); *A61M 16/0616* (2014.02); *A61M 2205/0205* (2013.01); *A61M 2205/0238* (2013.01); *A61M 2205/7527* (2013.01); *A61M 2205/7536* (2013.01); *C08J 2207/10* (2013.01); *C08J 2383/00* (2013.01); *C08J 2383/08* (2013.01); *C08L 41/00* (2013.01); *C08L 43/04* (2013.01)

(58) Field of Classification Search
CPC ... C08L 41/00; C08J 2383/08; C08J 2383/00; C08G 77/28
See application file for complete search history.

(56) References Cited

U.S. PATENT DOCUMENTS

| | | | |
|---|---|---|---|
| 3,159,601 A | 12/1964 | Ashby | |
| 3,159,662 A | 12/1964 | Ashby | |
| 3,220,972 A | 11/1965 | Lamoreaux | |
| 3,775,452 A | 11/1973 | Karstedt | |
| 4,767,794 A | 8/1988 | Modic | |
| 6,062,220 A | 5/2000 | Whitaker | |
| 7,069,932 B2 | 7/2006 | Busch | |
| 8,028,842 B2 | 10/2011 | McGrath | |
| 9,518,139 B2 * | 12/2016 | Burdinski | ........ C08J 5/18 |
| 2002/0160139 A1 | 10/2002 | Huang | |
| 2003/0005931 A1 | 1/2003 | Jaffre | |
| 2003/0106560 A1 | 6/2003 | Griesbach | |

(Continued)

FOREIGN PATENT DOCUMENTS

CN 101965209 A 2/2011
CN 101969871 A 2/2011
(Continued)

OTHER PUBLICATIONS

V.P. Barannikov et al, "Molecular Complexes of Crown Ethers in Crystals and Solutions", Russian Journal of Coordination Chemistry, vol. 28, No. 3, 2002, pp. 153-162.
(Continued)

*Primary Examiner* — Margaret G Moore
(74) *Attorney, Agent, or Firm* — Michael W. Haas

(57) ABSTRACT

Skin-contact products with a transpiration function such as medical devices or medicinal products, of which face masks, aspirators, ventilators, breast pumps or wound dressings are examples are described especially a skin-contact product with a transpiration function with an improved microclimate at a patient interface material-skin contact area. In an embodiment a material system is described that comprises a hydrophobic silicone base material and a hydrophilic silicone material that is combined with the hydrophobic base material.

3 Claims, 5 Drawing Sheets

(56) References Cited

U.S. PATENT DOCUMENTS

| | | |
|---|---|---|
| 2004/0025883 A1 | 2/2004 | Eaton |
| 2004/0068057 A1 | 4/2004 | Kim |
| 2006/0130842 A1 | 6/2006 | Kleman |
| 2007/0232767 A1* | 10/2007 | Ihata ............... C08F 10/00 526/172 |
| 2008/0047560 A1 | 2/2008 | Veliss |
| 2008/0091158 A1 | 4/2008 | Yang |
| 2009/0044810 A1 | 2/2009 | Kwok |
| 2009/0293880 A1 | 12/2009 | Rutan |
| 2010/0000544 A1 | 1/2010 | Blaszcykiewiez |
| 2010/0018534 A1 | 1/2010 | Veliss |
| 2010/0024811 A1 | 2/2010 | Henry |
| 2011/0158929 A1* | 6/2011 | Kim ............... C08F 220/06 424/70.16 |
| 2011/0209701 A1 | 9/2011 | Derringer |
| 2011/0294677 A1 | 12/2011 | Beckers |
| 2014/0113986 A1 | 4/2014 | Burdinski |
| 2014/0123981 A1 | 5/2014 | Willard |
| 2014/0134416 A1 | 5/2014 | Burdinski |

FOREIGN PATENT DOCUMENTS

| | | |
|---|---|---|
| DE | 10045183 A1 | 5/2002 |
| DE | 102009038655 A1 | 2/2011 |
| EP | 0054426 A2 | 6/1982 |
| EP | 179598 B1 | 4/1986 |
| EP | 0427474 A2 | 5/1991 |
| EP | 0796876 | 9/1997 |
| EP | 1314445 A1 | 5/2003 |
| EP | 2281595 A1 | 9/2011 |
| JP | 2006325688 A | 12/2006 |
| WO | WO1999157185 A1 | 11/1999 |
| WO | WO200287645 A1 | 11/2002 |
| WO | WO200712140 A1 | 2/2007 |
| WO | WO2008070929 A1 | 6/2008 |
| WO | 2009/024457 * | 2/2009 |
| WO | WO2009093174 A1 | 7/2009 |
| WO | WO2009109004 A1 | 9/2009 |
| WO | WO201096467 A1 | 8/2010 |
| WO | WO2010095105 A1 | 8/2010 |

OTHER PUBLICATIONS

"Which Mask Should I Choose to Protect Against Influenza?", Choosing an Influenza Masks, http://www.crghealthcare.com.au/choosing_a_mask.php, Downloaded Oct. 7, 2010, 1 Page.

"Face Mask With Sterile Visor", cleanroomshop.com, http://www.cleanroomshop.com/shop/2/12/index.htm, Downloaded Sep. 3, 2010, 4 Pages.

"The Performance Fabric", How the Aegis Microbe Shield Antimicrobial Kills Germs, http://www.breathehealthy.com/abouto-our-masks/the-breathe-healthy-technoloogy.html, Downloaded Sep. 3, 2010, 2 Pages.

Schneider et al, "Selectivity in Supramolecular Host-Guest Complexes", Chemical Society Reviews, vol. 37, 2008, pp. 263-277.

Creaven et al, "Coordination Chemistry of Calixarene Derivatives With Lower Rim Functionalisation and Their Appilcations", Coordination Chemistry Reviews, vol. 253, 2009, pp. 893-962.

Steed, "First-and Second-Sphere Coordination Chemistry of Alkali Metal Crown Ether Complexes", Coordination Chemistry Reviews, vol. 215, 2001, pp. 171-221.

Silicones, XP007918236, Encyclopedia of Polymer Science and Technology, vol. 11, 2003, pp. 765-841.

* cited by examiner

Material system in contact with skin
1. Hydrophobic silicone
2. Hydrophilic silicone with ~14.6 wt% sodium alpha-olefin sulfonate additive
1. Hydrophilic silicone with ~27.4 wt% sodium alpha-olefin sulfonate additive Material system in contact with skin
1. Hydrophobic silicone
2. Cotton
1. Silk

SKIN-CONTACT PRODUCT HAVING MOISTURE AND MICROCLIMATE CONTROL

CROSS-REFERENCE TO RELATED APPLICATIONS

This application is a Continuation of U.S. patent application Ser. No. 14/127,538, filed Dec. 19, 2013, now abandoned, which claims priority under 35 U.S.C. § 119(e) from provisional U.S. patent application No. 61/586,876 filed Jan. 16, 2012, and provisional U.S. patent application No. 61/502,961 filed Jun. 30, 2011, the contents of which are incorporated herein by reference.

BACKGROUND OF THE INVENTION

1. Field of the Invention

The present invention relates to skin-contact products with moisture and microclimate control such as medical devices or medicinal products, especially user or patient interface devices of which face masks, respiratory masks, aspirators, ventilators, breast pumps or wound dressings are examples and, more particularly, to a skin-contact product with a transpiration function with an improved microclimate at a patient interface-skin contact area.

2. Description of the Related Art

There are many medical applications which require gas exchange, e.g. pressure to be applied to the skin of a human or other animal over a long period of time where a microclimate is created that may be uncomfortable for the wearer. Examples are patient interface devices, respiratory masks, aspirators, ventilators, breast pumps, and wound dressings.

An exemplary medical application relates to a patient interface device used for ventilation for positive air pressure or oxygen delivery. Positive air pressure (PAP) is a method of respiratory ventilation used primarily for the treatment of sleep disorders such as obstructive sleep apnea (OSA). Sleep apnea is a sleep disorder characterized by abnormal pauses in breathing or instances of abnormally low breathing, during sleep. Each pause in breathing, called an apnea, can last from a few seconds to minutes, and may occur 5 to 30 times or more an hour. Similarly, each abnormally low breathing event is called a hypopnea. Sleep apnea is diagnosed with an overnight sleep test called a polysomnogram, or "sleep study". There are three forms of sleep apnea: central (CSA), obstructive (OSA), and complex or mixed sleep apnea (i.e. a combination of central and obstructive). In CSA, breathing is interrupted by a lack of respiratory effort; in OSA, breathing is interrupted by a physical block to airflow despite respiratory effort, and snoring is common.

A patient interface mask required to deliver PAP must have an effective seal and needs to be held on securely. A patient interface device is, for example, disclosed in the International patent applications WO2007/012140 and WO2008/070929. Many people find wearing the patient interface device uncomfortable to such an extent that use of the device is discontinued. Wearing a patient interface device, patients are reporting skin irritation, red marks and skin breakdown. The recovery time varies from minutes to hours but in extreme cases, longer-lasting skin damage and pressure sores can occur. These skin problems result in low patient compliance with patient interface devices and CPAP therapy.

The root causes for formation of red marks in the face of a person wearing a patient interface device are manifold and not yet fully understood. Common factors reported in tissue breakdown are excessive mechanical skin load by pressure, shear and friction.

In general, mechanical skin loading by pressure, shear and friction can lead to multiple effects:
  Ischemia: the occlusion of capillary blood vessels.
  Reperfusion injury: after unloading, accumulated free radicals are released and cause inflammation and cell damage.
  Lymphatic function impairment: occlusion and damage of the lymph vessels prevents the removal of metabolic waste, leading to tissue necrosis.
  Mechanical deformation of tissue cells: cell membranes rupture, volume changes of cells leads to initial damage, and cytoskeletal reorganization occurs.
  Moisture accumulation in the skin due to coverage of the skin decreases the skin strength to damage.

The materials of choice in current patient interface devices, such as PAP patient interface masks, are silicone rubbers because of the biocompatibility they provide. Silicone materials, a group of materials based on various types of polysiloxanes, are typically highly stable against chemical modification and aging and, therefore, guarantee for a long shelf life and time of use.

Silicone rubbers can be made via three different major industrial methods. The platinum salt catalyst induced method (applicable to vinyl and SiH containing silicone prepolymers) is the preferred method as it gives medical grade materials. The two other methods, i.e. peroxide crosslinking of vinyl-containing silicone prepolymers or tin salt catalyst induced crosslinking of silanol containing silicone prepolymers, are less preferred for skin contacting areas but can be option for other, non skin contacting parts of the patient interface. These materials are intrinsically hydrophobic and have very low water permeability, and, thus, do not provide a suitable environment for growth of bacteria and harmful bio-films. As a result of these properties, silicone materials can function as a tight seal in those areas of a person's face, where they are in contact with the skin. These are typically all areas in which a patient interface device contacts the face. While a tight seal is desired, the hydrophobic materials are not very suitable to allow transport of moisture and sweat, which attributes to the red mark formation and discomfort.

As another example, a wound dressing is known with which a screen is placed over substantially the whole surface of the wound. The size and configuration of the screen can be adjusted to fit the individual wound. It can be formed from a variety of porous semi-rigid materials. The material must be sufficiently porous to allow oxygen to reach the wound, and sufficiently rigid to prevent wound overgrowth, for example the use of an open-cell polymer foam is known. Some designs of wound dressing require direct connection of the screen to a vacuum pump through a flexible hose inserted into the foam. Such foam can vary in thickness and rigidity, although it is preferred that a spongy material be used for the patient's comfort if the patient must lie upon the device during its operation.

The molecular design and synthesis of hydrophilic silicone materials is a relatively unexplored area. Still, some hydrophilic silicone materials have been disclosed in the known prior art. For example, patent application publication No. US2002/0160139 discloses a surface modified polymer including a surface that is covalently bonded to a surface modifying compound. Formation of the covalent bond between the polymer and the surface modifying compound is achieved by a reaction between an intrinsic functional group that is present in the polymer and the functional group of the surface modifying compound. By using a polymer having an intrinsic functional group, a separate surface activation step is avoided. Thus, the material has a hydrophilic surface while the bulk of the material remains hydrophobic. Accordingly, this material does not allow for the uptake of moisture or diffusion of moisture through the material and moisture can, thus, not be removed effectively from a contact area.

Another known prior art example in the field of hydrophilic silicone materials is International patent application WO2010/905105, which discloses a novel microfluidic system having a substrate based on rubber material having polar side groups that are linked to the rubber polymer backbone via a spacer. This arrangement provides for a transport of water-based fluids such as blood or saliva by capillary forces. The provided material has a hydrophilic surface as well as hydrophilic bulk properties allowing for a beneficial use in microfluidic devices intended for use with aqueous solutions. The rubber material includes polar side groups that are linked with the polymer chain of the rubber material via a carbon chain (linker) comprising at least 6 atoms. The rubber material is made by a process including the step of radical addition of a suitable rubber precursor monomer with anionic precursor material. By doing so, the rubber material may be produced relatively easy. The step of radical addition may be performed, for example, by radical dimerization of alkene moieties or by any other known bonding technique in the field. It may be performed by a radical initiator, such as peroxides or tin organyls, or by UV-light. More specifically, the polar side groups may be ionic side groups such as —SO3-. For instance the material may be a silicone rubber modified with 15-20 w % sodium alkene $C_{14-16}$ sulfonate. The silicone rubber may have a chain length from 1000 to 10000 Si—O units, and the modified silicone rubber may be made by radical addition of ω-alkenylsulfonic acids to siloxane units present in the polysiloxane chain.

More generally, many commercial polymers are not skin friendly as they do not absorb water or sweat from the skin.

Introduction of an alpha-olefin sulfonate surfactant into these polymers may provide a copolymer with an increased hydrophilic character which can be used to increase its biocompatibility and its capacity to hold water. For the manufacture of skin-contact products, this is especially relevant to biocompatible polymers such as, but not limited to, silicones, polybutadiene, polybutadiene-containing polymers, polybutadiene-polyethylene oxides copolymers, poly (meth)acrylates, and isobutylene-ethylene glycol copolymers.

However alpha-olefin sulfonate surfactants, although having a vinyl functional group, do not easily mix with the monomer of commercial polymers like polyethylene (PE), polypropylene (PP), polybutadiene, polyisoprene, polystyrene (PS), polyacetonitrile (PAN), silicones, poly(meth)acrylates, polyacrylonitrile, acrylonitrile-butadiene-styrene copolymers (ABS) and styrene-acrylonitrile copolymers (SAN). This incompatibility can be due to differences in boiling points, making these non volatile surfactants nearly impossible to use in gas phase polymerizations. Even under liquid phase polymerization conditions, it is difficult to mix a hydrophilic surfactant containing a sulfonic acid salt with a hydrophobic monomer or pre-polymer. Only in a special case like the suspension polymerization of vinyl chloride in water, can the hydrophilic surfactant be dissolved in a part of the reaction mixture (water) and thus incorporated into the main polymer. However polyvinyl chloride is not regarded as a skin-compatible polymer.

Despite this effort, there is still a need for an improved microclimate at a device-skin contact area, which is well suited to reduce moisture accumulation in the skin, which decreases skin strength, and ultimately the formation of red marks. Further, there is also a need for a wider range of polymer materials, in particular silicone rubber materials, with hydrophilic bulk properties for use as an aid to moisture control, in particular for manufacturing devices with moisture control properties like face masks, such as patient interface masks for positive air pressure (PAP) therapy of obstructive sleep apnea (OSA), and wound dressings.

SUMMARY OF THE INVENTION

It is a principal object of embodiments of the present invention to provide a skin-contact product with moisture and microclimate control such as medical devices or medicinal products, health care or safety or emergency products, of which user or patient interface devices, respiratory masks, aspirators, ventilators, breast pumps or wound dressings are examples. The moisture and microclimate control can be provided by materials in contact with the skin having a transpiration function.

An advantage of a skin-contact product with moisture and microclimate control according to embodiments of the present invention is the provision of an improved microclimate at a material skin interface, e.g. when used in a user interface device. This can be achieved by using a material system for the product, e.g. for a user or patient interface device that reduces moisture accumulation in and on the skin. The special feature of this skin contact product is that due to the microclimate control, moisture increase at the interface of the skin and skin contact product as well as stratum corneum hyper-hydration can be prevented. In this way the decrease of the tensile strength of the skin due to moisture uptake can be prevented.

The skin contact product thus contributes to tissue tolerance to shear stress and friction and thus to less damage of the skin for example during wearing a user or patient interface device. The skin contract product thus improves comfort of a user or patient interface device and supports the reduction of red mark formation and skin irritation for example if a patient interface mask is applied to the skin.

The object of the invention can be achieved by making use of material systems that include composites of different materials or material systems with well defined material stacks, with which moisture uptake as well as moisture penetration may be realized in the material while providing improved product stability on the skin.

In one aspect the present invention provides skin contact product such as a user interface adapted for use in a system for communicating a flow of gas with a user, the user interface comprising a user contacting assembly having a first portion comprising (1) a support material, and (2) a contact structure comprising moisture uptake means that is non-releasably combined with and supported by the support material, wherein the contact structure is adapted so that the moisture uptake means at least partially contacts a skin surface of a user responsive to the user interface being worn by such a user wherein the support material provides mechanical and dynamical stability for the moisture uptake means, or the first portion of the user contact assembly, and wherein the moisture uptake means allows for uptake or diffusion of moisture from a skin surface of a user over which the user contacting assembly is disposed.

In accordance with embodiments of the present invention user contacting assembly can reduce moisture accumulation, irritation and red mark formation when in contact with the skin of a person and in this way improves comfort. In any of the embodiments of the present invention, moisture uptake means or any other part of the device may include anti-bacteria, and anti fungi agents such as silver compounds, or an anti-viral agent such as a microbiocide, all or any of these being in or coated on any material in contact with the skin of the user.

The moisture uptake means can be provided by a variety of materials or material systems such as a hydrophilic material that absorbs water, a hydrophilic material formed with capillaries which take up water, a hydrophobic material formed with capillaries which take up water, etc. The take up of water into the material can result in softening or weakening of the material and the support material has the purpose of supporting such weakened material. Hence the moisture uptake means can comprise a hydrophilic material or a hydrophobic material depending on how it is structured and used. In embodiments the hydrophilic material can be a textile integrated in the contact structure. Preferably such a material is adapted so that said textile at said skin surface of a user is crease-free and/or leak-free. The hydrophilic material can be a rubber material that takes up at least 5% by weight of water, preferably more that 10% by weight of water and particularly preferably more than 40% up to 120% by weight of water, or up to 200% or up to 250% or up to 500% by weight of water after immersion in demineralized water at room temperature for a sufficient time such as 5 days or more to reach saturation. It is expected that with increasing water absorption the mechanical properties may be reduced such that a support material is not only necessary but must be designed in a form that will stabilise the hydrophilic material.

Hence, the interface may comprise a support portion, the first portion being operatively coupled to the support portion. This support portion may be a shell, such as a transparent shell or dome. This may cover the mouth, the nose, the mouth and nose of the patient. The support portion can be form stable. The support portion can be adapted to receive a gas connection for gas exchange which can be either pressurised gas such as air or a vacuum or both. Hence, a gas transfer port or a gas exchange port may be located in the support portion for the purposes of communicating a gas flow.

Communicating a gas flow means that a gas pressure is developed that can be either a positive or negative pressure. To avoid loss or leak of gas, a seal can be provided for forming a gas exchange sealing contact with skin of a user. This seal may be integrated into user contacting assembly or may be separate.

In embodiments the support material comprises a hydrophobic material or a hydrophilic material, preferably a rubber material. The rubber material can be any of silicone, latex, and polybutadiene or other materials as disclosed below.

In accordance with a further embodiment of the present invention, and following similar guiding principles as for the user interface device hereinabove, there is also provided a wound dressing, e.g. a wound dressing with the application of vacuum, comprising a hydrophilic rubbery or elastomeric polymer material taking up at least 5% by weight of water, and up to 500% by weight of water after immersion in demineralized water at room temperature for a sufficient time to reach saturation.

In further embodiments of the present invention hydrophilic polymer materials are provided, e.g. hydrophilic rubber or elastomeric materials, other than a hydrophilic silicone rubber material. This may be achieved for example by providing a hydrophilic polyurethane. Hydrophilic polyurethanes can be made by coupling a diisocyanate monomer or pre-polymer with hydrophilic monomers or pre-polymers. Examples of such hydrophilic monomers or pre-polymers include, but are not limited to, glycerol, ethylene glycol derivatives, polyethylene glycol and other hydroxyl function-containing polyol compounds. The hydrophilic properties can be even further increased by coupling a hydrophilic polyurethane with another hydrophilic polymer which does not necessarily contain a hydroxyl group. The hydrophilic material can be any of: hydrophilic silicone, polyvinylpyrrolidones (usually with a number average molecular weight from 20,000 to 400,000), poly(hydroxyethyl methacrylates), polyethylene glycols (usually with a number average molecular weight from 200 to 10,000), polyvinyl alcohols (usually with a number average molecular weight from 10,000 to 150,000), polyacrylamides, alkali metal poly (meth)acrylates (such as, but not limited to, sodium polyacrylate, potassium polyacrylate, sodium polymethacrylate, potassium polymethacrylate), and mixtures thereof or other materials as disclosed below.

In any of the embodiments of the present invention the hydrophilic material moisture uptaking means, or any other part of the device, may include one or more anti-bacterial agents, and/or one or more anti fungal agents such as silver compounds, or one or more anti-viral agents such as a microbiocide, all or any of these being for instance present in, or coated onto, any material in contact with the skin of the user.

In one embodiment of the present invention, said hydrophilic material is a hydrophilic silicone material and the hydrophobic material is a hydrophobic silicone material.

In another embodiment of the present invention said support material is a hydrophobic material that forms a base layer;
  wherein said hydrophilic material is a hydrophilic silicone that forms a first layer disposed over the base layer; and
  wherein said first layer is adapted to be disposed against the skin of a user responsive to the user interface being worn by such a user.

In yet another embodiment of the present invention, said hydrophilic material is mixed into said support material, said support material being a hydrophobic material to form a composite mixture.

In a further embodiment of the present invention, a layer of hydrophobic material is formed at an outside of said composite mixture;
  wherein said layer is perforated forming apertures; and
  wherein said apertures are for contacting said hydrophilic material with the skin of a person.

In still another embodiment of the present invention, said support material is a hydrophobic material that includes a plurality of holes positioned at an interface of said hydrophobic material for contacting the skin of a person;
  wherein said holes are filled with said hydrophilic material; and
  wherein said hydrophilic material is for contact with the skin of a person.

The user interface described in the present invention can be made in a variety of forms and may comprise a forehead pad and/or a nose/mouth cushion. Generally there will be means for securing the interface in place, e.g. tapes, straps, bands etc which can be adjustable.

In various embodiments the support portion can be in the form of a shell having a rim, and wherein the user contacting assembly is attached to the rim in a sealed manner.

Preferably the support material is stiffer than said hydrophilic material when there has been uptake of moisture in said hydrophilic material.

The user interface can be for use in a variety of systems such as system for communicating a flow of gas with an airway of a user.

In particular embodiments of the present invention, the user interface device or the wound dressing make use of a hydrophilic rubber material instead of, or in combination with, the typical hydrophobic rubber material, e.g. hydrophilic silicone material instead of or in combination with the typical hydrophobic silicone material. The hydrophilic rubber material preferably takes up more than 5% by weight of water, preferably more than 10% by weight of water, particularly preferably more than 20% and preferably more than 40% by weight up to 120% by weight of water, or up to 200% by weight of water, up to 250% by weight of water, or up to 500% by weight of water after immersion in demineralized water at room temperature for a sufficient amount of time, such as 5 days or more, to reach saturation. In accordance with embodiments of the present invention user contacting assembly can reduce moisture accumulation, irritation and red mark formation when in contact with the skin of a person and in this way improves comfort. In any of the embodiments of the present invention, moisture uptake means or any other part of the device may include one or more anti-bacterial agents, and/or one or more anti fungal agents such as silver compounds, or one or more anti-viral agents such as a microbiocide, all or any of these being either present in or coated onto any material in contact with the skin of the user.

Accordingly, in one embodiment in accordance with the present invention, a combination of hydrophobic and hydrophilic materials such as, but not limited to, a combination of hydrophobic and hydrophilic silicone materials, near the product-skin interface is utilized. The combination can be used with a shell or enclosure, such as an airtight enclosure that is part of a user or patient interface device or mask or similar. The enclosure can be made of rigid material or can be a semi-rigid material having some flexibility provided it forms a form-stable enclosure. Such an enclosure can have a rim that forms a seal with the skin, e.g. a seal such as required for aspiration, ventilation etc. of a person, or for the application of vacuum in a wound dressing. Hence the seal generally only needs to be suitable for positive or negative pressures (pressures up to 70 KPa and more). For example, a flap can extend around a rim or perimeter of the patient interface device and can be made of a relatively flexible material to provide a leak resistant seal over the patient contacting area. However, according to embodiments, of the present invention at least part of the hydrophilic material e.g. hydrophilic silicone material may be arranged such that, in use, it is in contact with the skin of a person. The hydrophobic material such as hydrophobic silicone material can be adapted to ensure mechanical stiffness of the product having a user interface, such as a patient interface device or face mask. The hydrophilic material such as hydrophilic silicone material is adapted to allow transport of moisture and sweat to improve comfort, prevent moisture accumulation at the skin and stratum corneum hyper-hydration and prevent decrease of the tensile strength of the skin. The material thus supports reduction of red mark formation, skin irritation, skin damage if applied to the skin as e.g. patient interface device.

In one embodiment in accordance with the present invention, a layer of a hydrophilic material such as hydrophilic silicone material is placed on top of a hydrophobic material such as hydrophobic silicone material such that it comes in contact with the skin of a person using the skin-contact product having a user interface. The contact can be suitable for forming a seal as mentioned above. In another embodiment in accordance with the invention, the hydrophobic material such as hydrophobic silicone material includes openings in a surface that is in contact with the skin of a person during the use of the skin-contact product having a user interface, the openings being filled with hydrophilic material such as hydrophilic silicone material. The contact can be suitable for forming a seal as mentioned above. In yet another embodiment in accordance with the invention, hydrophobic and hydrophilic materials such as hydrophobic and hydrophilic silicone materials are mixed resulting in some of the hydrophobic material and some of the hydrophilic material ending up at the skin-product cushion interface. The contact can be suitable for forming a seal as mentioned above. As can be seen, in each of these embodiments in accordance with the invention, at least part of the hydrophilic material such as hydrophilic silicone material is in contact with the skin of a person during the use of the skin-contact product having a user interface, such as a face mask. In each case, the skin contact can be suitable for forming a seal.

A water-absorbing rubbery or elastomeric polymer material useful as a component of a user interface device or a wound dressing according to the present invention may be present under various forms. For instance it may be in the form of a sheet, or a fiber, or a coating adapted for adhesion to a substrate, or a foam, e.g. a foam with a foam density from 60 to 300 kg/m$^3$.

It is a further and independent object of further embodiments of the present invention to provide novel compositions for the preparation of hydrophilic silicone materials allowing for improved mixing and synthesis processes resulting in improved hydrophilic bulk properties of the obtained hydrophilic silicone material. Such materials can be suitable for use in a skin-contact product with moisture and microclimate control such as a medical device or a medicinal product, of which face masks, aspirators, ventilators, breast pumps or wound dressings are examples.

Such a hydrophilic material may allow for an effective removal of moisture from any user interface where it is used, for example from the skin-mask interface areas or from other devices such as wound dressings, by either uptake of the moisture in the hydrophilic silicone material or by diffusion of the moisture through the hydrophilic silicone away from the contact area. As a result, an improved microclimate at the skin-product interface areas is created, which may be well suited to improve comfort, reduce skin irritation, reduce skin damage by less moisture accumulation and ultimately reduce the formation of red marks.

In a further and independent object of further embodiments of the present invention, the hydrophilic materials is another material than a hydrophilic silicone material, for example hydrophilic polyurethanes. Hydrophilic polyurethanes are made by coupling the diisocyanate monomer or pre-polymer with hydrophilic monomers or pre-polymers. Examples of hydrophilic monomers or pre-polymers are glycerol, ethylene glycol derivatives, polyethylene glycol and other hydroxyl function containing poly-ol compounds. The hydrophilic properties can be even further increased by coupling this small chain hydrophilic polyurethane with other hydrophilic polymers which do not necessarily contains a hydroxyl group. Examples of these more general hydrophilic polymers are: polyvinylpyrrolidones (usually with a number average molecular weight from 20,000 to 400,000), poly(hydroxyethyl methacrylates), polyethylene glycols (usually with a number average molecular weight from 200 to 10,000), polyvinyl alcohols (usually with a number average molecular weight from 10,000 to 150,000), polyacrylamides, alkali metal poly(meth)acrylates (such as, but not limited to, sodium polyacrylate, potassium polyacrylate, sodium polymethacrylate, potassium polymethacrylate), and mixtures thereof. In accordance with embodiments of the present invention user contacting assembly can reduce moisture accumulation, irritation and red mark formation when in contact with the skin of a person and in this way improves comfort. In any of the embodiments of the present invention, hydrophilic materials may include anti-bacteria, and anti fungi agents such as silver compounds, or an anti-viral agent such as a microbiocide, all or any of these being in or coated on any material in contact with the skin of the user.

In a further and independent object of further embodiments of the present invention, the hydrophilic materials is yet another material such as a textile based material, in which the fiber content is inherently moisture absorbing such as cellulose fibers (cotton, viscose) or silk and wool. Alternatively moisture absorption can be achieved due to the textile structure such as woven, knitted, non-woven, or other engineered fabrics such as spacer fabric.

In this embodiment the patient interface is either made fully out of the textile based material to take moisture up and reduce red marks or it can be a hybrid material with for example based on a rubber such as a silicone rubber combined with one or more layers of textile. To be able to achieve the object of the invention, the present invention provides a hydrophilic rubber material that takes up more than 5% by weight of water, preferably more that 10% by weight of water and particularly preferably more than 20% by weight and preferably more than 40% by weight or even up to 120% by weight of water, or up to 200% by weight of water, up 250% by weight of water, or 500% by weight of water after immersion in demineralized water at room temperature for a sufficient amount of time at room temperature, such as 5 days or more, to reach saturation.

It is thus a further and independent object of further embodiments of the present invention to provide hydrophilic polymer materials, e.g. hydrophilic rubber or elastomeric materials, other than a hydrophilic silicone rubber material. This may be achieved for example by providing a hydrophilic polyurethane. Hydrophilic polyurethanes can be made by coupling a diisocyanate monomer or pre-polymer with hydrophilic monomers or pre-polymers. Examples of such hydrophilic monomers or pre-polymers include, but are not limited to, glycerol, ethylene glycol derivatives, polyethylene glycol and other hydroxyl function-containing polyol compounds. The hydrophilic properties can be even further increased by coupling a hydrophilic polyurethane with another hydrophilic polymer which does not necessarily contain a hydroxyl group. Examples of such hydrophilic polymers include, but are not limited to: polyvinylpyrrolidones (usually with a number average molecular weight from 20,000 to 400,000), poly(hydroxyethyl methacrylates), polyethylene glycols (usually with a number average molecular weight from 200 to 10,000), polyvinyl alcohols (usually with a number average molecular weight from 10,000 to 150,000), polyacrylamides, alkali metal poly(meth)acrylates (such as, but not limited to, sodium polyacrylate, potassium polyacrylate, sodium polymethacrylate, potassium polymethacrylate), and mixtures thereof.

Such a hydrophilic rubber material may be obtained by a process comprising the steps of (a) providing a silicone precursor and a hydrophilic molecule or polymer, and (b) polymerizing said silicone precursor in the presence of said hydrophilic molecule or polymer and in the optional presence of a solvent.

In this process the silicone precursor may or may not react with the hydrophilic polymer.

With respect to hydrophilic silicone rubber materials that do not contact the skin or a mucosa, there is no limitation upon the manufacturing method by which they may be obtained, that is any of the three crosslinking methods briefly mentioned above and further detailed hereinafter may be suitable, depending upon the medical or non-medical application for which the hydrophilic silicone rubber material is intended, and depending the form (e.g. sheet, coating, fiber or foam) in which the water-absorbing silicone rubber material is desired.

The peroxide cross-linking method can give non medical grade hydrophilic silicone rubbers by adding vinyl containing hydrophilic molecules, for example an ethylenically unsaturated (olefinic) soap such as an alpha-olefinic sulfonic acid sodium salt, to the silicone mixture. Other reactive groups suitable for this reaction are allyl, acrylic or methacrylic groups. The ethylenically unsaturated (olefinic) soap can directly be added to the mixture and will thus be incorporated into the silicone matrix by the radical cross-linking reaction, e.g. see scheme 1 showing a simplified non-limiting overview of the peroxide cross-linking of a vinyl-containing silicone prepolymer with vinyl containing hydrophilic molecules. In this scheme, $R_1$ and $R_3$ each designate residue groups of the peroxide used to initiate cross-linking. $R_2$ is a hydrogen atom, an alkyl group or a trimethylsilyl group.

Scheme 1

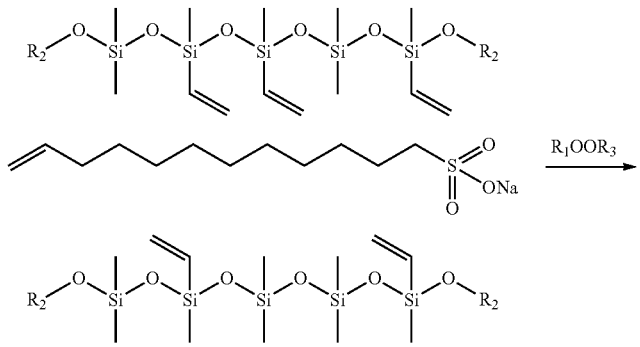

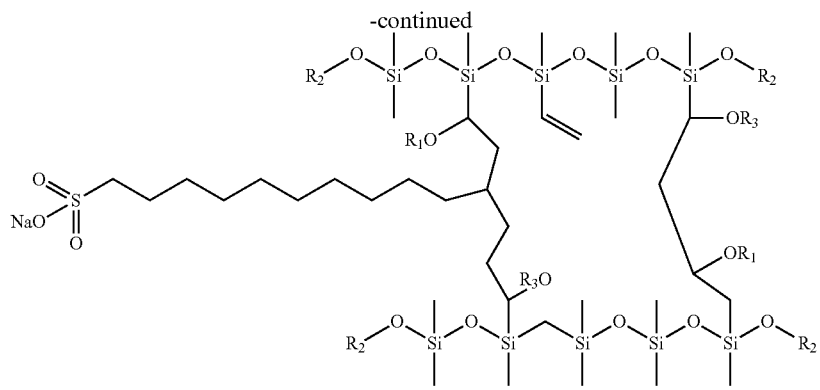

Suitable peroxides ($R_1OOR_3$) for this crosslinking reaction include, but are not limited to, for instance dicumyl peroxide, bis(2,4-dichlorobenzoyl) peroxide or 2,5-bis-(tert.-butylperoxo)-2,5-dimethylhexane. As this cross-linking polymerization is based on radicals several hydrophilic or silicone containing molecules may be incorporated into the silicone matrix.

Non medical grade hydrophilic silicone rubbers can also be made by a tin catalyzed condensation polymerization but here the hydrophilic molecules need to contain a hydrolysable silane group. Suitable hydrolysable silanes preferably contain one or more alkoxy or acetoxy groups which are able to react in the silanol condensation reaction. As an example, a suitable molecule is 3-(trihydroxysilyl)-1-propanesulfonic acid (CAS 70942-24-4) for instance commercially available from Gelest Inc. (Morrisville, Pa., USA), but molecules with other hydrophilic groups such as trialkoxysilane terminated polyglycols are also possible. Scheme 2 below shows a simplified overview of the tin catalyzed cross linking of silanol containing silicone prepolymers with hydrophilic molecules with an alkoxy- or acetoxysilane group. In this scheme, $R_1$ is H or a hydrolysable group like an alkoxy or an acetoxy group.

Scheme 2

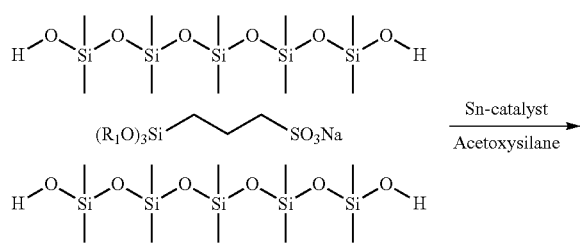

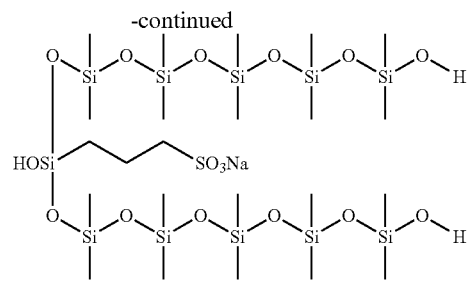

The third method is the preferred method to make medical grade silicone rubbers but can also be used for non medical applications. The present invention more specifically relates to hydrophilic silicone-based rubber materials having such high water uptake capacity at room temperature that they can be used for manufacturing skin-contact products, in particular skin-contact products with a transpiration function. In other embodiments, the water-absorbing (hydrophilic) silicone-based rubber materials of the present invention are suitable for contact with the mucosa of a human.

The present invention also relates to polymerizable compositions comprising both hydrophobic and hydrophilic monomers that can be polymerized under liquid phase polymerization conditions, and to polymers and copolymers that can be obtained from such compositions. The present invention more specifically relates to biocompatible polymers and copolymers comprising both hydrophobic and hydrophilic monomer units. The hydrophilic monomer units can be incorporated in the main chain or as a side group of the silicone polymer matrix. Incorporation into the main chain is possible when the hydrophilic molecules contain two or more active groups which can react in the cross-linking reaction. Possible molecules are sulfonic acid salt with two or more vinylic groups or hydrophilic polymers with two or more side or terminal groups containing a double bond like an allyl group. A schematic overview of this reaction is given in scheme 3 showing the incorporation of hydrophilic molecules into the silicone rubber matrix main chain, wherein the hydrophilic molecule has two reactive groups that can participate in the platinum catalyzed crosslinking reaction, and wherein a suitable reactive group is an allyl group. Incorporation as a side group is possible when the hydrophilic molecule contains only one reactive group that can react in the cross-linking reaction.

Scheme 3

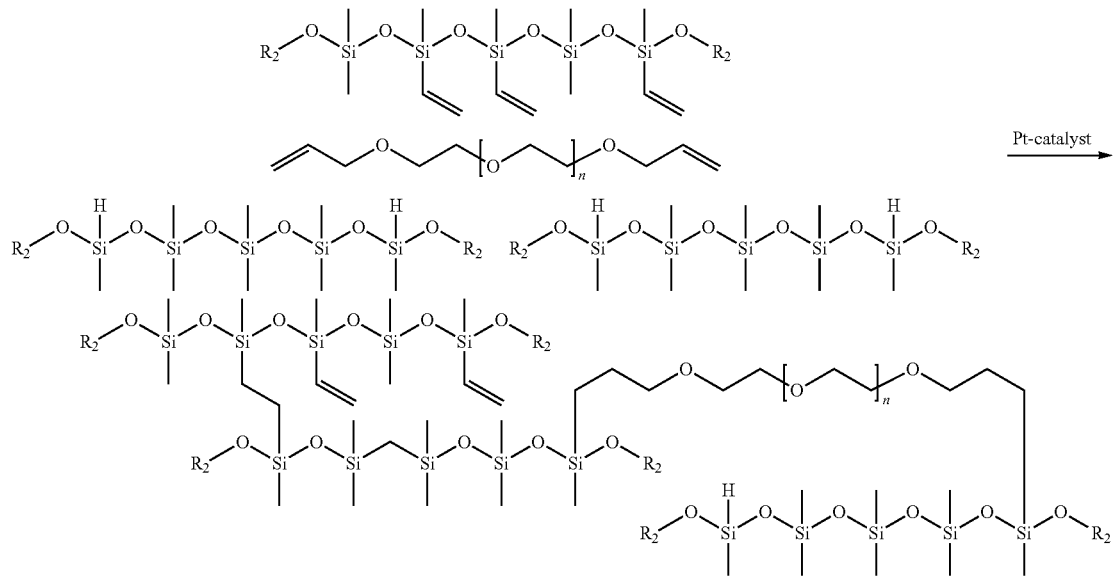

In one embodiment of the present invention, a hydrophilic silicone-based rubber material comprises:
   dialkylsiloxane (preferably dimethylsiloxane) and/or arylsiloxane (preferably methylphenyl siloxane or diphenylsiloxane) repeating units, and
   at least one modified dialkylsiloxane or modified arylsiloxane repeating unit wherein one alkyl or aryl group of said repeating unit is replaced with a hydrophilic side group,
   and is such that the total number of repeating units (a) and repeating units (b) is at least 5 and less than 1,000. The repeating units (a) form part of what is hereinafter called a "silicone precursor". The repeating units (a) may be of a single type (e.g. preferably dimethylsiloxane), or mixed types (e.g. dimethylsiloxane and diphenylsiloxane) in any proportions. In the latter case, they may be arranged randomly in the polymer chain, or they may be arranged in the form of block copolymers, for instance polydiphenylsiloxane-polydimethylsiloxane-polydiphenyl-siloxane tri-block copolymers.

In a broader aspect, it is a principal object of other embodiments of the present invention to provide a rubber or elastomeric material taking up more than 5% by weight of water and up to 120% by weight of water, or up to 200% by weight of water, up 250% by weight of water, or 500% by weight of water after immersion in demineralized water at room temperature for a sufficient amount of time, such as 5 days or more, to reach saturation, comprising:
   (a) repeating units from one or more hydrophobic organic monomers, and
   (b) repeating units from one or more monomers (a) being modified with one or more hydrophilic side groups.

Said polymer material may be any rubbery or elastomeric polymer material, e.g. one wherein said hydrophobic organic monomer (a) is selected from the group consisting of butadiene, isoprene, dialkylsiloxanes, diarylsiloxanes, acrylic acid alkyl esters, acrylonitrile, chloroprene, fluorinated ethylene, mixtures of ethylene and vinyl acetate, mixtures of ethylene and one or more acrylic acid esters, and mixtures of ethylene with propylene and a diene.

In one embodiment of the present invention, a rubbery polymer material may be one wherein said hydrophobic organic monomer (a) is a dialkylsiloxane or a diarylsiloxane, and wherein the total number of repeating units (a) and repeating units (b) is at least 5 and less than 1,000.

In one embodiment of the present invention, said polymer material may be one wherein said hydrophilic side groups are ionic side groups such as, but not limited to, C3-C28 alkylsulfonate groups in association with a cation. Said cation may be a monovalent cation selected from the group consisting of ammonium and alkali metal (Li, Na, K) cations, or a divalent cation selected from the group consisting of alkaline-earth metal cations (Ca, Mg). Other hydrophilic side groups can also comprise at least one moiety from ionic groups such as sulfate (—OSO3-), phosphate (—OPO3 2-), phosponate (—PO3 2-), carboxylate (—CO2-), ammonium (NR1R2R3R4+), or phosphonium (PR1R2R3R4+) or combinations of these groups like in betaine (R1R2R3N+—CR4R5-CO2-) or sulfobetaine (R1R2R3N+—CR4R5-SO3-). It can also contain non ionic hydrophilic groups like alcohol groups such as hydroxy (—OH), glycols (—OCH2CH2OH), or sugar derivates, ethers such as glycol ether (—(OCH2CH2-)nOR), amines (—NR1R2), amides (—CONR1R2), phosphine oxide (—POR1R2), aldehydes (—CHO) or esters (—COOR). Preferred counter ions comprise the before mentioned ammonium, alkali, earth alkali ions, H+ or mixtures and for the positive hydrophilic side chains the preferred counter ions are the halogenides (F—, Cl—, Br—, I—), hydroxide (OH—), acetate (CH3COO—), sulfite (SO32-), sulfate (SO42-), nitrite (NO2-), nitrate (NO3-), phosphate (PO43-), perchlorate (ClO4-) or tetrafluorborate (BF4-) or mixtures thereof.

In one embodiment of the present invention, said rubbery or elastomeric polymer material may be one wherein the repeating units (b) represent from 1% to 30% for instance from 2% to 25%, or from 3% to 20%, or from 5% to 15%, of the total number of repeating units (a) and repeating units (b). The proportion of repeating units (b) present in the water-absorbing rubbery or elastomeric polymer material may be appropriately selected by the skilled person depending upon parameters such as, but not limited to, the type of repeating units (b), the desired level and kinetics of water uptake, and the kind of medical device or non-medical device, or part thereof, comprising said rubbery or elastomeric polymer material.

In one embodiment of the present invention, said rubbery or elastomeric polymer material may further comprise a detectable amount of a ligating compound or ligand. Said ligating compound or ligand may be a cyclic compound such as, but not limited to, a crown ether, a cryptand or a calixerene.

It is a principal object of other embodiments of the present invention to provide a polymerizable composition suitable for producing a rubbery or elastomeric polymer material such as recited herein-above, said composition comprising:
(a) one or more hydrophobic organic monomers or pre-polymers,
(b) one or more hydrophilic monomers capable of modifying said hydrophobic organic monomers or pre-polymers (a) especially under liquid phase polymerization conditions, being a C3-C28 alkenyl sulfonate in association with a cation, and
(c) a ligating compound or a solvent in an amount sufficient to increase solubility or miscibility of said hydrophilic monomers (b) in said hydrophobic organic monomers or pre-polymers (a) under polymerization conditions.

The hydrophobic organic monomers or pre-polymers (a) may be biocompatible in view of medicinal applications of the resulting polymer.

In further embodiments of this invention, the hydrophilic monomer (b):
may react or associate with said ligating compound or solvent (c),
after reaction or association with said ligating compound or solvent (c), may be able to react with said hydrophobic organic monomers or pre-polymers (a) under liquid phase polymerization conditions, and/or
may be incorporated into the polymer sequence resulting from liquid phase polymerization of said hydrophobic organic monomers or pre-polymers (a).

The preferred polymerization method is the platinum-salt catalyzed method as this gives medical grade materials.

In one embodiment of the present invention, the hydrophilic side group of said repeating units (b) may be an alkenyl sulphonate having from 3 to 28 (preferably 10 to 18, more preferably 12 to 16) carbon atoms in association with a cation. Said cation may be a monovalent cation selected from the group consisting of ammonium and alkali metal cations (such as, but not limited to, the cations of Li, Na, or K). Said cation may also be a divalent cation selected from the group consisting of alkaline-earth metal cations (such as the cations of Ca or Mg).

In one embodiment of the present invention, the hydrophilic side group of said repeating units (b) may be derived from a hydrophilic polymer selected from the group consisting of polyvinylpyrrolidones (usually with a number average molecular weight from 20,000 to 400,000), poly(hydroxyethyl methacrylates), polyethylene glycols (usually with a number average molecular weight from 200 to 10,000), polyvinyl alcohols (usually with a number average molecular weight from 10,000 to 150,000), polyacrylamides, alkali metal poly(meth)acrylates (such as, but not limited to, sodium polyacrylate, potassium polyacrylate, sodium polymethacrylate, potassium polymethacrylate), and mixtures thereof.

In one embodiment of the present invention, the polymer material may be a (partially) hydrophilic silicone-based rubber material wherein the molar ratio of the repeating units (a) to the repeating units (b) is at least 4.5, preferably at least 7, more preferably at least 9, most preferably at least 13. In one embodiment of the present invention, the polymer material may be a (partially) hydrophilic silicone-based rubber material wherein the molar ratio of the repeating units (a) to the repeating units (b) is at most 90, preferably at most preferably 40, most preferably at most 25.

In one embodiment of the present invention, the (partially) hydrophilic silicone-based rubber material may be a mixture of hydrophilic silicone rubber material and the hydrophilic molecule or polymer.

In one embodiment of the present invention, the (partially) hydrophilic silicone-based rubber material has an exceptionally high water uptake capacity, for instance it may take up more than 5% by weight (preferably more than 10% by weight, more preferably more than 15% by weight, most preferably more than 20% by weight, of water after immersion in demineralized water at room temperature for a sufficient time such as 5 days or more to reach saturation. The hydrophilic silicone-based rubber material of the invention may take up at most 120% by weight, at most 200% by weight, at most 250% by weight, or at most 500% by weight of water after immersion in demineralized water at room temperature for a sufficient time such as 5 days or more to reach saturation (see FIG. 6).

In one embodiment of the present invention, the polymer material may be a (partially) hydrophilic silicone-based rubber material further comprising residual traces or detectable amounts of a ligating compound or ligand that may be used during the process for its preparation. For instance when said hydrophilic side group is an alkenyl sulfonate having from 3 to 28 (preferably 10 to 18, more preferably 12 to 16) carbon atoms in association with a cation, said compound may be a cyclic ligand such as, but not limited to, a crown ether, a cryptand or a calixarene. Although there are effective procedures for removing a ligand such as a crown ether or a cryptand from a hydrophilic silicone-based rubber material of this invention, such as heating under vacuum, however it may be unnecessary to completely remove said ligand and residual but still detectable traces of the ligand may be admissible for medicinal applications. Methods for detecting and quantifying the presence of ligating compounds, such as crown ethers or cryptands, in a polymer material such as a (partially) hydrophilic silicone-based rubber material of the present invention are well known to the person skilled in the art.

In further embodiments of the present invention are provided processes for making the novel silicone-based rubber materials described herein. In one embodiment of the present invention, a first process for preparing a hydrophilic silicone-based rubber material comprises the steps of:
(a) providing a silicone precursor and one or more hydrophilic monomers (preferably a vinyl-terminated hydrophilic monomer) or polymers; and
(b) polymerizing said silicone precursor in the presence of said hydrophilic monomers or polymers, until obtaining a hydrophilic silicone-based rubber material which takes up more than 5% by weight (preferably more than 10% by weight, more preferably more than 15% by weight, most preferably more than 20% by weight) of water and at most up to 120% by weight of water, or up to 200% by weight of water, up 250% by weight of water, or 500% by weight of water after immersion in demineralized water at room temperature for a sufficient time such as 5 days or more to reach saturation. vels.

In one embodiment of the present invention, a second process for preparing a hydrophilic silicone-based rubber material comprises the steps of:
(a) providing a silicone precursor and one or more hydrophilic ionic monomers (preferably a vinyl-terminated hydrophilic ionic monomer) or polymers;
(b) polymerizing said silicone precursor in the presence of said hydrophilic ionic monomers or polymers and in the further presence of a ligating compound or solvent.

In one embodiment of the present invention, a third process for preparing a hydrophilic silicone-based rubber material comprises the steps of:
(a) providing a silicone precursor having Si—O repeating units, wherein the number of Si—O repeating units in said silicone precursor is at least 5 and less than 1000,
(b) providing one or more hydrophilic monomers (preferably a vinyl-terminated hydrophilic monomer) or polymers; and
(c) polymerizing said silicone precursor in the presence of said hydrophilic monomers or polymers.

In one embodiment of each of the three above processes of the present invention, said silicone precursor may react with said hydrophilic monomers (preferably a vinyl-terminated hydrophilic monomer) or polymers. In particular said reaction may be via addition of a vinyl group onto a silicon-hydrogen bond.

In one embodiment of each of the three above processes of the present invention, said silicone precursor bears reactive Si—H groups with a spacer group between said reactive Si—H groups, which preferably comprises at least 5 and less than 1,000 silicon atoms interspersed with oxygen atoms.

In one embodiment of each of the three above processes of the present invention, said hydrophilic monomer may be an alpha-olefin or alkenyl sulfonate having 3 to 28 (preferably 10 to 18, more preferably 12 to 16) carbon atoms in association with a cation. Said cation may be a monovalent cation selected from the group consisting of ammonium and alkali metal cations (such as, but not limited to, the cations of Li, Na, or K). Said cation may also be a divalent cation selected from the group consisting of alkaline-earth metal cations (such as the cations of Ca or Mg).

Other hydrophilic side groups can also comprise at least one moiety from ionic groups such as sulfate (—OSO3-), phosphate (—OPO3 2-), phosponate (—PO3 2-), carboxylate (—CO2-), ammonium (NR1R2R3R4+), or phosphonium (PR1R2R3R4+) or combinations of these groups like in betaine (R1R2R3N+—CR4R5-CO2-) or sulfobetaine (R1R2R3N+—CR4R5-SO3-). It can also contain non ionic hydrophilic groups like alcohol groups such as hydroxy (—OH), glycols (—OCH2CH2OH), or sugar derivates, ethers such as glycol ether (—(OCH2CH2-)nOR), amines (—NR1R2), amides (—CONR1R2), phosphine oxide (—POR1R2), aldehydes (—CHO) or esters (—COOR). Preferred counter ions comprise the before mentioned ammonium, alkali, earth alkali ions, H+ or mixtures and for the positive hydrophilic side chains the preferred counter ions are the halogenides (F—, Cl—, Br—, I—), hydroxide (OH—), acetate (CH3COO—), sulfite (SO32-), sulfate (SO42-), nitrite (NO2-), nitrate (NO3-), phosphate (PO43-), perchlorate (ClO4-) or tetrafluorborate (BF4-), or mixtures thereof.

In one embodiment of each of the three above processes of the present invention, said hydrophilic polymer may be selected from the group consisting of polyvinylpyrrolidones (usually with a number average molecular weight from 20,000 to 400,000), poly(hydroxyethyl methacrylates), polyethylene glycols (usually with a number average molecular weight from 200 to 10,000), polyvinyl alcohols (usually with a number average molecular weight from 10,000 to 150,000), polyacrylamides, alkali metal poly(meth)acrylates (such as, but not limited to, sodium polyacrylate, potassium polyacrylate, sodium polymethacrylate, potassium polymethacrylate), and mixtures thereof.

In one embodiment of each of the three above processes of the present invention, said silicone precursor reacts with said hydrophilic monomer or polymer in the presence of a ligating compound or a solvent. The ligating compound may be a cyclic ligating compound such as, but not limited to, a crown ether, a cryptand or a calixarene, for instance a crown ether capable of dissolving the cation associated with the alpha-olefin or alkenyl sulfonate having 3 to 28 (preferably 10 to 18, more preferably 12 to 16) carbon atoms.

A suitable crown ether may depend upon the atomic size of the cation. In one embodiment of the present invention, the cation is a lithium ion and the crown ether is a 12-crown-4 crown ether. In one embodiment of the present invention, the cation is a sodium ion and the crown ether is a 15-crown-5 crown ether. In one embodiment of the present invention, the cation is a potassium ion and the crown ether is a 18-crown-6 crown ether.

In place of a ligating compound, a solvent may be used to assist dissolution of the alkenyl sulfonate into the siloxane precursor. In one embodiment of the present invention, the solvent has a very low boiling point below 100° C. In another embodiment of the present invention, the solvent may be a ketone (such as, but not limited to, acetone), another polar solvent (such as, but not limited to, chloroform), a low boiling alcohol (such as, but not limited to, ethanol) or a mixture of said low boiling alcohol with water. In another embodiment of the present invention, the solvent may have a higher boiling point, for instance between 100° C. and 300° C., to provide a more stable mixture during the total production process. This higher boiling solvent can be an aliphatic alcohol such as, but not limited to, isopropanol, hexanol or decylalcohol, an aliphatic ether such as, but not limited to, an ethylene- or propylene-glycol ether or di- and trimers of ethylene or propylene glycol, a ketone such as, but not limited to, methylethyl ketone, methylpropyl ketone or cyclohexanone, a chlorinated solvent such as, but not limited to, trichloroethylene, tetrachloroethylene or (di)chlorobenzene or any other polar solvent.

In one embodiment of each of the three above processes of the present invention, the hydrophilic silicone-based rubber material comprises at least one material represented by the following structural formula:

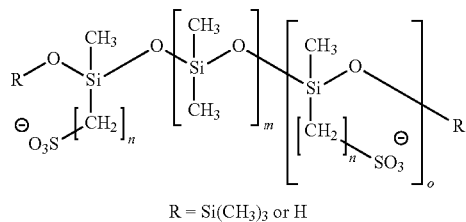

R = Si(CH3)3 or H wherein n is from 3 to 28 (preferably 10 to 18, more preferably 12 to 16) and wherein the total number (m+o+1) of repeating units is at least 5 and less than 1,000, with n and o being integers independently selected from each other and preferably being at least 6. In the above structural formula, the terminal end groups R usually consist of Si(CH3)3 and/or hydrogen.

In one embodiment of the present invention, the hydrophilic silicone-based rubber material comprises at least one material represented by the above structural formula, wherein the molar ratio m/o is at least 4.5, preferably at least 7, more preferably at least 9, most preferably at least 13. In one embodiment of the present invention, the hydrophilic silicone-based rubber material comprises at least one material represented by the above structural formula, wherein the molar ratio m/o is at most 90, preferably at most preferably 40, most preferably at most 25.

In one embodiment of the present invention, a hydrophilic silicone material comprises a silicone precursor material, a sodium alpha-olefin sulfonate, and a crown ether mixing mediator that facilitates mixing of the sodium alpha-olefin sulfonate with the silicone precursor material. The silicone precursor material may be a commercial silicone elastomer material such as, but not limited to, Elastosil LR 3004/40 from Wacker Silicones (Germany). The sodium alpha-olefin sulfonate is also a commercially available product, or may be produced according to methods well known in the art. The crown ether may be a 15-crown-5 ether. In one embodiment of the present invention, the hydrophilic silicone material includes from 40 to 98.5% by weight of the silicone precursor material, from 1 to 30% by weight of the sodium alpha-olefin sulfonate, and up to 30% by weight of the mixing mediator, and it takes up from 1 to 85% by weight of water after immersion in demineralized water for 5 days at room temperature.

In a further embodiment of the present invention, a method for manufacturing a hydrophilic silicone material includes the steps of: mixing a sodium alpha-olefin sulfonate with an a component of a silicone precursor material and with a crown ether or solvent mixing mediator, adding a silicone precursor B component, mixing again, and obtaining a hydrophilic silicone mixture. The method for manufacturing a hydrophilic silicone material includes standard production techniques with steps: casting or molding the hydrophilic silicone mixture, curing the hydrophilic silicone mixture, and obtaining the hydrophilic silicone material. The method for manufacturing a hydrophilic silicone material includes further the steps of: mixing the sodium alpha-olefin sulfonate with silicone precursor material and with the mixing mediator. Also mixing of hydrophilic silicone and sodium alpha-olefin without mediator is possible. The method for manufacturing a hydrophilic silicone material includes further the steps of: providing a commercial sodium alpha-olefin sulfonate, providing a commercial silicone elastomer as the silicone precursor material, and providing a 15-crown-5 ether as the mixing mediator. The method for manufacturing a hydrophilic silicone material includes further the step of performing the mixing at room temperature.

In a more general aspect, the present invention provides a process for preparing a rubbery or elastomeric polymer material, comprising the steps of:
   providing one or more hydrophobic organic monomers,
   providing one or more hydrophilic monomers or polymers, and
   polymerizing said hydrophobic organic monomers in the presence of said hydrophilic monomers or polymers until obtaining a rubbery or elastomeric polymer material wherein repeating units from the one or more hydrophobic organic monomers are modified with hydrophilic groups from said one or more hydrophilic monomers or polymers, said rubbery or elastomeric polymer material taking up more than 5% by weight of water and at most 120% by weight of water, up to 200%, up to 250% or up to 500% weight of water after immersion in demineralized water at room temperature for a sufficient time, such as 5 days or more, to reach saturation.

In a further embodiment of this general method of the present invention, polymerization occurs in the presence of a ligating compound or a solvent for said hydrophilic monomer or polymer. In one embodiment of the present invention said ligating compound is a crown ether, a crypt- and or a calixarene such as described herein-above. In one embodiment of the present invention, the solvent has a very low boiling point. In another embodiment of the present invention, the solvent may be a ketone (such as, but not limited to, acetone), another polar solvent (such as, but not limited to, chloroform), a low boiling alcohol (such as, but not limited to, ethanol) or a mixture of said low boiling alcohol with water. In another embodiment of the present invention, the solvent may have a higher boiling point, for instance between 100° C. and 300° C., to provide a more stable mixture during the total production process. This higher boiling solvent can be an aliphatic alcohol such as, but not limited to, isopropanol, hexanol or decylalcohol, an aliphatic ether such as, but not limited to, an ethylene- or propylene-glycol ether or di- and trimers of ethylene or propylene glycol, an aliphatic ketone such as, but not limited to, methyl ethyl ketone, methyl propyl ketone or cyclohexanone, a chlorinated solvent such as, but not limited to, trichloroethylene, tetrachloroethylene or (di)chlorobenzene or any another polar solvent.

In a still further embodiment of the present invention, the hydrophilic silicone material is used in a material system in combination with a hydrophobic silicone base material. At least a part of the hydrophilic material is in contact with a moist surface. The hydrophobic base material provides mechanical and dynamical stability of the material system. The hydrophilic material allows for uptake of moisture and diffusion of moisture away from the moist surface. The moist surface may be skin of a person. In one embodiment of the invention, the hydrophobic base material forms a base layer and the hydrophilic material forms a top layer placed above the base layer. In another embodiment of the present invention, the hydrophilic material is mixed into the hydrophobic base material to form a composite mixture, a layer of hydrophobic base material is formed at an outside of the composite mixture, the layer is perforated forming apertures, and the apertures connect the hydrophilic material with the moist surface. In still another embodiment of the invention, the hydrophobic base material includes a plurality of holes positioned at an interface of the hydrophobic base material with the moist surface, the holes are filled with the hydrophilic material, and the hydrophilic material is in contact with the moist surface.

In a still further embodiment of the present invention, the material system is utilized to fabricate a skin-contact product such as, but not limited to, a patient interface material of a patient interface device. The moist surface is skin of a person wearing the face mask. The mask material can be, for example, integrated in a patient interface mask for positive air pressure therapy of obstructive sleep apnea. The hydrophobic silicone base material provides mechanical and dynamical stability of the patient interface device and the hydrophilic silicone material allows for uptake and diffusion of moisture away from a patient interface device-skin interface. The patient interface material reduces moisture accumulation, stratum corneum hyper-hydration and thus contributes to tissue tolerance to shear stress and thus to less damage of the skin for example during wearing a patient interface device. The skin contract product thus improves comfort of a patient interface device and supports the reduction of red mark formation and skin irritation for example if a patient interface mask is applied to the skin.

BRIEF DESCRIPTION OF THE DRAWINGS

The present invention will now be described, by way of example, with reference to the accompanying drawings, in which.

Corresponding reference characters indicate corresponding parts throughout the several views. The exemplification set out herein illustrates exemplary embodiments of the invention, in one form, and such exemplification is not to be construed as limiting the scope of the invention in any manner.

DETAILED DESCRIPTION OF EXEMPLARY EMBODIMENTS

1. Definitions

Figure 1:
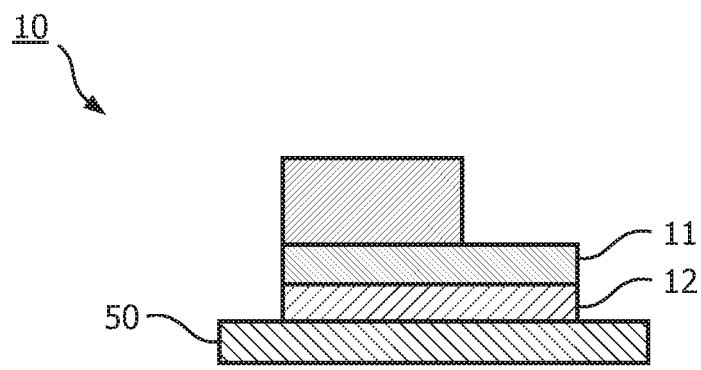
FIG. 1 is a schematic cross-sectional view of a material system with defined layers of hydrophilic and hydrophobic silicone materials in accordance with one embodiment of the present invention.

Hydrophobic materials are characterized by a water contact angle that is larger than that of hydrophilic materials. The larger the contact angle, the more hydrophobic is the material, the smaller the contact angle, the more hydrophilic is the material. Hydrophilic materials are defined herein as materials that allow the uptake and/or diffusion of water.

Examples of hydrophobic materials are silicone rubbers, natural rubbers, polyalkene polymers like polyethylene and polypropylene, fluorine-containing polymers like Teflon, oils, waxes etc. In the context of the various embodiments of the present invention, preferred hydrophobic materials are hydrophobic silicones and natural rubbers.

Examples of hydrophilic materials are natural fabrics like cotton, silk or wool, hydrogels as used in contact lenses or diapers, water soluble polymers like polyvinylalcohol, polyethylene glycols, natural polymers like proteins (gelatin) or polysaccharides (agar agar, mucins) and hygroscopic inorganic compounds like zeolites, zeolite based components or salts. In the context of the various embodiments of the present invention, preferred hydrophilic materials are hydrophilic silicones, with a crosslinking structure and/or crosslinking density comparable to that of suitable hydrophobic materials, which may be combined in a single composite material. Hydrophilic silicones have a normal silicone backbone but instead of hydrophobic methyl or phenyl groups some of these groups are exchanged for more hydrophilic side groups. Hydrophilic side groups contain, for example, alcohol, carboxylic acid, amine, amide and ethylene glycol functional groups.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. Where an indefinite or definite article is used when referring to a singular noun e.g. "a" or "an", "the", this includes a plural of that noun unless something else is specifically stated.

The term "comprising", used in the claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

The present invention relates to skin-contact products with moisture and microclimate control such as medical devices or medicinal products, especially patient interface devices of which face masks, aspirators, ventilators, breast pumps or wound dressings are examples and, more particularly, to a skin-contact product with moisture and microclimate control with an improved microclimate at a skin interface. The invention will mainly be described with reference to a user or patient interface device, such as a face mask, as this medical application involves the basic elements of the present invention:

a) contact with the skin over a period of time, e.g. several hours,
b) pressure areas on the skin,
c) a material in direct contact with the skin,
d) formation of a microclimate on areas of the skin,
e) a requirement of at least a transpiration function, i.e. sweat or moisture from the skin must be allowed to migrate from the skin, and f) Gaseous materials may need to be communicated or exchanged through a material part of the device such as air or oxygen for breathing or air or oxygen in a wound dressing. Other gases may be communicated for special uses, e.g. anesthetics.

These characteristics are common to user interface devices such as respiratory masks used by firefighters, patient interface devices, such as respiratory masks, face masks, breast pumps or wound dressings or other health care products.

The skin-contact product may include an enclosure or shell such as is typical for a user or patient interface device or mask. A user or patient interface device may include a mask shell having a contact portion or cushion attached to the shell that contacts the surface of the patient. The mask shell and cushion are typically held in place by a headgear that wraps around the head of the patient or person. The mask and headgear form the user or patient interface assembly. A typical headgear includes flexible, adjustable straps that extend from the mask to attach the mask to the patient or person.

The enclosure or shell can be made of rigid material or of a semi-rigid material e.g. a flexible material that is sufficiently form stable. An example is polycarbonate plastic. Such an enclosure or shell can have a rim that forms a seal with the skin at its rim, e.g. a seal such as required for aspiration, ventilation etc. of a person when using a user or patient interface device. such as a mask or can be for the application of vacuum in a wound dressing. For example, a flap can extend around a rim or perimeter of the patient interface device and can be made of a relatively flexible material to provide a leak resistant seal over the patient contacting area.

Because such patient interface devices can be worn for an extended period of time, a variety of concerns must be taken into consideration. For example, in some treatments, the person or patient wears the user or patient interface device all day when they work (e.g. a firefighter) or all night long while he or she sleeps. One concern in such a situation is that the patient interface device is as comfortable as possible, otherwise the patient may avoid wearing the interface device, defeating the purpose, e.g. to protect against fumes or to provide the prescribed pressure support therapy. When used facially, it is also important that the interface device provide a tight enough seal against a user's or patient's face without discomfort. A problem arises in that in order for the user or patient interface device to maintain a seal without any undue gas leaks around its periphery, the patient interface device may be compressed against the patient's face.

Figure 9:
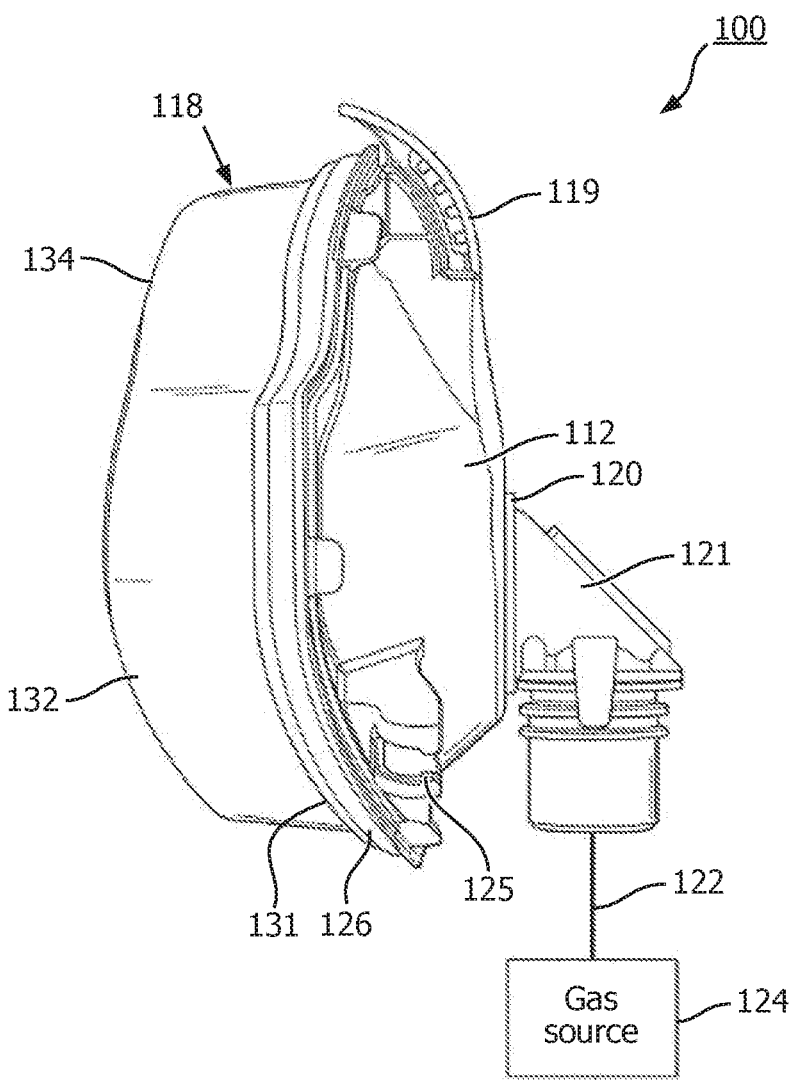
FIG. 9 shows an exemplary user or patient interface that can be used with the present invention.

Accordingly and referring to FIG. 9, there is generally indicated at 100, a user interface device such as a patient interface device which can be used with the present invention including a body or shell 112 having a first side that defines a generally annular surface to which is sealingly coupled a cushion 118. Shell 112 is preferably, although not necessarily, a generally rigid shell, and can be transparent whereas cushion 118, in the illustrated embodiment, is a flexible, resilient member that will be described in greater detail hereinafter. Cushion 118 according to embodiments of the present invention comprises a support material 132, and a contact structure 134 comprising moisture uptake means that is non-releasably combined with and supported by the support material 132, wherein the contact structure 134 is adapted so that the moisture uptake means at least partially contacts a skin surface of a user responsive to the user interface being worn by such a user wherein the support material provides mechanical and dynamical stability for the moisture uptake means, or the first portion of the user contact assembly, and wherein the moisture uptake means allows for uptake or diffusion of moisture from a skin surface of a user over which the contacting assembly is disposed.

Shell 112 also defines an opening 120 to which, in the illustrated embodiment, there is connected a fluid coupling device such as a gas transfer port, e.g. a swivel coupling 121 for carrying fluid, such as a breathing gas, between a chamber within the mask and an external gas source. It is to be understood that with the present invention a variety of fluid coupling devices can be attachable, either permanently or selectively, to opening 120 to carry fluid to or from the chamber defined by user or patient interface device 100. In the illustrated embodiment, opening 120 and intervening coupling 121 connect user or patient interface device 100 via a conduit, which is represented by line 122, to a source of gas 124, e.g., a blower or other suitable device, for providing a flow of pressurized breathing gas, for example, for administration of the gas to a user. Coupling 121 preferably includes exhaust vents which exhaust exhaled gases in a known manner. The present invention contemplates that an exhaust vent can be any conventional exhaust vent, and can be located on the mask, such as on the mask shell, on the patient circuit, at the mask shell/patient circuit interface, or at any combination of such locations. The exhaust vent can be as described in published U.S. application Ser. No. 10/119,673, entitled, "Exhaust Port Assembly for a Pressure Support System," Publication No. US 2003 0005931, the contents of which are incorporated herein by reference.

In the illustrated embodiment, cushion 118 is preferably attached to shell 112 using ring 126 in a known manner. The cushion may include a first end portion that couples to the mask shell. The first end portion can be generally triangular shaped and attaches to similarly-shaped opening provided in a second side of the mask shell. The mask shell and the first end portion of the seal that attaches thereto can be both generally planer, i.e., both lies in a linear plane. It should be noted that the present invention contemplates that the mask shell and the first end portion of the seal can be contoured, when viewed in profile, so that first end portion, for example, does not lie in a common plane.

It is to be further understood that the present invention contemplates using any conventional technique for attaching the first end portion of the cushion to the mask shell. Such techniques include permanently bonding the cushion to the mask shell, for example, using adhesives, mechanical fasteners, or molding the cushion onto the shell such that the cushion is selectively detachable from the mask shell. When coupled to the mask shell, the cushion can define a chamber for receiving a portion of the user or patient when the mask is donned by the user or patient. Typically, a part of the user or patient, such as the user's or patient's nose, inserts into the chamber so that the user's or patient's airway is in fluid communication with the chamber.

The cushion can include a second end portion for sealing engagement with a face of a patient. A sidewall can be provided that extends between first end portion and second end portion. The cushion can be a unitary structure that attaches to a mounting portion of a mask shell or other support structure and provides a surface at second end portion that contacts a surface of a patient. In the case of a nasal mask, for example, the second end portion contacts the area of the user or patient generally around the nose including over the bridge of the nose.

Source of gas 124 is any device that provides gas to the user. The gas source may include an oxygen supply, a ventilator, a pressure support device, such as a CPAP device, a variable pressure device, e.g., a BiPAP®, Bi-Flex, or C-Flex device manufactured and distributed by Respironics, Inc. of Pittsburgh, Pa., or an auto-titration pressure support system. A BiPAP, Bi-Flex, or C-Flex device is a pressure support device in which the pressure provided to the patient varies with the patient's respiratory cycle, so that a higher pressure is delivered during inspiration than during expiration. An auto-titration pressure support system is a system in which the pressure varies with the condition of the patient, such as whether the patient is snoring or experiencing an apnea, hypopnea, flow limited breathing, upper airway resistance, or snoring.

The user or patient interface device 100 shown is a full or an oral/nasal mask that accommodates both the mouth and nasal regions of the user's face. It is to be understood, however, that the present invention also contemplates a nasal mask that accommodates both the nasal regions of a user or a total face mask that accommodates substantially the entire facial area of the patient. It should also be understood that the illustrated embodiments are examples only of masks using the materials of the present invention and that the present invention is not limited to the embodiments described herein. Embodiments of the present invention include a respiratory mask including a shell and seal, can have any one of an infinite number of configurations, shapes, and sizes. The shell can correspond to that described in U.S. application Ser. No. 10/654,379, entitled, "Patient Interface With Forehead Support System," the contents of which are incorporated herein by reference. The mask shell is preferably formed from rigid plastic, such as polycarbonate. As described in detail in the '379 application the mask can include an adjustable forehead support.

The forehead support can be generally T-shaped and can include a support arm, which is slideably connected to a forehead support bracket. The forehead support bracket includes a forehead pad disposed on the patient contacting side to engage the forehead of the user. It is to be understood that the present invention contemplates that the forehead support assembly, and its individual components, can have anyone of a variety of configurations. The present invention also contemplates that the forehead support assembly can be eliminated entirely.

A headgear can be used to attach to the mask via headgear clips. Headgear clips can attach to headgear straps, for example by inserting the headgear straps into slots provided on the clips. The headgear clips are selectively attachable to the mask shell in any conventional manner. The headgear clips attach to each side of forehead support bracket and to each side of the lower portion of the mask shell. It can thus be appreciated that the headgear and head clip can have any configuration so as to be selectively attachable to the mask. It is to be further understood that the present invention contemplates eliminating all, or a portion, of the headgear clips an attaching the headgear straps to the mask shell. For example, in the illustrated embodiment, the lower corners of shell 112 also include headgear attaching elements in the form of receiving socket attachment elements 125 which cooperate with corresponding ball elements (not illustrated) on headgear straps. The ball and socket configuration, and other headgear attachment configurations suitable for use with the present invention, are disclosed in co-pending U.S. patent application Ser. No. 10/629,366, (publication no. US-2004-0025883-A1) the contents of which are incorporated herein by reference. It is to be understood, however, that the present invention contemplates using any conventional connection assemblies to attach a headgear to mask shell 112 in this or any of the other embodiments.

The present invention contemplates the headgear 119 that can be used with user or patient interface device 100 can be any suitable headgear, i.e., any conventional headgear used in the user or patient interface field. For example, a typical headgear assembly comprises a headpiece that overlies a portion of the user or patient's crania and with headgear straps extending therefrom to adjustably connect the headgear to the mask.

Referring now to FIG. 1, material for a contact structure comprising moisture uptake means that is non-releasably combined with and supported by a support material will be described. A material system 10 with defined layers of hydrophilic and hydrophobic materials is illustrated in accordance with one embodiment of the present invention. The materials in embodiments of the present invention are preferably hydrophilic and hydrophobic silicone materials. Alternative hydrophilic materials are for example polyurethanes but also moisture uptaking textiles such as cotton, silk or polyester with defined structure or hydrophobic textiles with hydrophilic coating. Alternative hydrophobic materials are latex or polybutadien.

Preferably a rubber or elastomeric material is used to provide a sufficient seal. At this moment there only a few rubber materials commercially available: natural rubber (latex), silicone rubber, rubbers based on butadiene or butadiene containing compounds (examples are isoprene, halogenated butadiene and mixtures with butadiene (nitrile rubber, styrene rubber)) and special rubbers like perfluorinated rubbers (Viton) and acrylate rubbers. Silicone rubbers are preferred as they are very compatible with the skin and can be molded in any form.

Hydrophilic polyurethanes are made by coupling the diisocyanate monomer or pre-polymer with hydrophilic monomers or pre-polymers. Examples of hydrophilic monomers or pre-polymers are glycerol, ethylene glycol derivatives, polyethylene glycol and other hydroxyl function containing poly-ol compounds. The hydrophilic properties can be even further increased by coupling this small chain hydrophilic polyurethane with other hydrophilic polymers which do not necessarily contains a hydroxyl group. Examples of these more general hydrophilic polymers are: polyvinylpyrrolidones (usually with a number average molecular weight from 20,000 to 400,000), poly(hydroxyethyl methacrylates), polyethylene glycols (usually with a number average molecular weight from 200 to 10,000), polyvinyl alcohols (usually with a number average molecular weight from 10,000 to 150,000), polyacrylamides, alkali metal poly(meth)acrylates (such as, but not limited to, sodium polyacrylate, potassium polyacrylate, sodium polymethacrylate, potassium polymethacrylate), and mixtures thereof.

In embodiments of the present invention a user contacting assembly is provided having a first portion comprising:
    (a) a support material, and
    (b) a contact structure comprising moisture uptake means that is non-releasably combined with and supported by the support material, wherein the contact structure is adapted so that the moisture uptake means at least partially contacts a skin surface of a user responsive to the user interface being worn by such a user wherein the support material provides mechanical and dynamical stability for the moisture uptake means, and wherein the moisture uptake means allows for uptake or diffusion of moisture from a skin surface of a user over which the patient contacting assembly is disposed.

In the following a selection of embodiments are described to illustrate aspects of the present invention but these are only examples and the skilled person will realise that alternatives thereto are included within the scope of the present invention. The embodiments provide various material systems that comprise a plurality of materials which in combination provide the support material, and the contact structure.

In particular in one embodiment a material system 10 includes a hydrophobic material base layer 11 and a hydrophilic material top layer 12. Hydrophilic material top layer 12 is in contact with a moist surface, such as skin 50. Hydrophilic material top layer 12 comprises or consists of intrinsically hydrophilic material. The stiffness of hydrophilic materials can depend strongly on the water content. Typically, hydrophilic materials exhibit lower stiffness at higher water content. High water content occurs for for hydrophilic materials which show a good water permeability. Therefore, hydrophilic material top layer 12 may be combined with hydrophobic material base layer 11 by placing layer 12 on top of layer 11. Thus, layer 12 may allow for penetration or uptake of moisture from skin 50 by utilizing the hydrophilic nature of the polymers molecular framework or by allowing for passage of moisture through the material through dedicated-channels. Accordingly, moisture accumulation in skin 50 may be prevented.

Figure 4A:
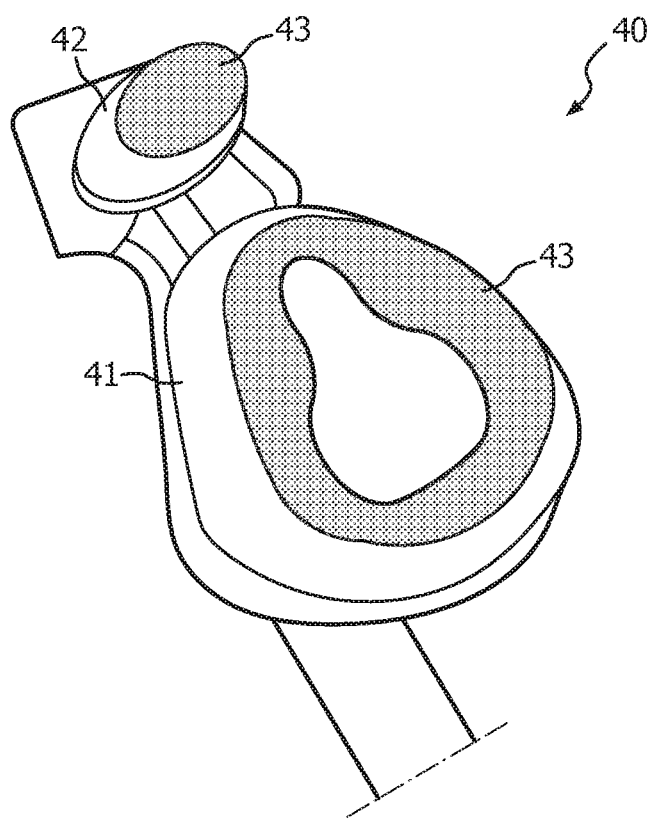
FIGS. 4a and 4b are perspective views of an exemplary patient interface device or face mask in accordance with the various embodiments of the present invention.

Material system 10 may be, for example, utilized to fabricate an interface material such as a user or patient interface device material such as a cushion 41 and a forehead pad 42 or any other material in the mask in contact with the skin of a user interface or patient interface device 40, as illustrated in FIG. 4a. The user interface, and, therefore, face mask 40, may be, but is not limited to, a PAP patient interface mask. Other applications for material system 10 may include, for example, respiratory patient interface devices, gas masks, pressurized masks, or diving masks. Skin 50 may be the skin of a person, such as a patient receiving PAP treatment, wearing face mask 40. The patient interface device or mask material 41 may be made in a standard way but also any technology to realize the patient interface devices material can be used. However, instead of filling a mold completely with hydrophobic injection molding material as done in the prior art, the mold may be filled with base layer 11 of a hydrophobic material, such as a hydrophobic silicone material, and a top layer 12 of a hydrophilic material, such as a water free hydrophilic silicone material. Top layer 12 may be preferably positioned at a patient interface device material-skin interface 43 that comes in contact with skin 50 when a patient interface device 40 is worn by a person.

Accordingly, a face mask 40, such as a PAP patient interface device, with a standard stiffness and a water absorbing and water permeable patient interface material-skin interface 43 may be fabricated utilizing material system 10 in accordance with an embodiment of the present invention.

Figure 4B:
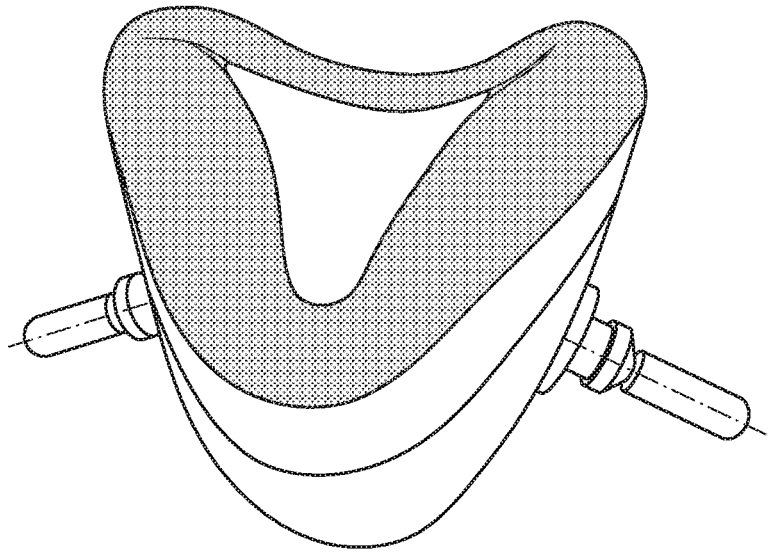

For example, a flap can extend around a rim or perimeter of the patient interface device and can be made of a relatively flexible material to provide a leak resistant seal over the patient contacting area. Alternatively, by utilizing material system 10 an airtight seal may be formed at material-skin contact area 43 allowing for the use of overpressure. An example of such a face mask with a hydrophilic silicone layer 12 processed on top of a hydrophobic silicone part 11 by compression molding is shown in FIG. 4b.

The stiffness of face mask 40 provided by hydrophobic material base layer 11 may be such that patient interface 40 withstands the overpressure. An improved microclimate at mask material-skin contact area 43 may be provided by hydrophilic material top layer 12.

Figure 2:
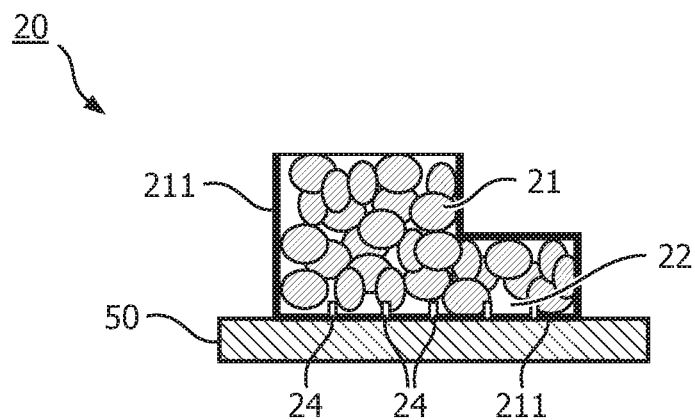
FIG. 2 is a schematic cross-sectional view of a material system with a two phase compound of hydrophilic and hydrophobic silicone materials in accordance with another embodiment of the present invention.

Referring now to FIG. 2, material system 20 with a two phase compound of hydrophilic and hydrophobic materials is illustrated in accordance with one embodiment of the present invention. Material system 20 includes a hydrophobic base material 21 and hydrophilic material 22 mixed into hydrophobic base material 21. The outside of material system 20 may be formed of hydrophobic base material 21, which may be perforated to include apertures 24. Apertures 24 may connect hydrophilic material 22 with a moist surface, such as skin 50. Material system 20 may by a composite mixture, where at least one hydrophilic material 22 is combined with at least one hydrophobic base material 21. Hydrophilic material 22 may allow for uptake and/or diffusion of moisture away from the interface of material system 20 with skin 50. Hydrophobic base material 21 may provide the mechanical and dynamical stability of material system 20.

Material system 20 may be, for example, utilized to fabricate a user or patient interface cushion, such as a cushion 41 and a forehead pad 42 of a user interface or patient interface, such as face mask 40, as illustrated in FIG. 4. The user interface, and, therefore, face mask 40 may be, but is not limited to, a PAP patient interface mask. Other applications for material system 20 may include, for example, respiratory masks, gas masks, pressurized masks, or diving masks. Skin 50 may be the skin of a person, such as a patient receiving PAP treatment, wearing face mask 40. Patient interface device cushion 41 may be made from a composite mixture of hydrophobic base material 21, such as a hydrophobic silicone material, and hydrophilic material 22, such as a water free hydrophilic silicone material. The ratio between the hydrophobic base material 21 and the hydrophilic material 22 may be chosen such that mask 40 has the required stiffness. The components of material system 20 may phase separate during crosslinking to form a water-absorbing and a water-repelling phase. The outer surface of mask cushion 41 or forehead pad 42 may be covered with a layer 211 of hydrophobic base material 21 as these have the lowest surface energy. Afterwards, layer 211 may be perforated to form apertures 24 that enable water absorption from skin 50 in the hydrophilic material 22.

In this embodiment of a composite material of hydrophilic and hydrophobic the layer 211 is optional.

By utilizing material system 20 in accordance with an embodiment of the present invention, an airtight seal may be formed at patient interface material skin contact area 43 allowing for the use of overpressure. The stiffness of face mask 40 provided by hydrophobic base material 21 may be such that face mask 40 withstands the overpressure. An improved microclimate at patient interface material-skin contact area 43 may be provided by hydrophilic material 22.

Figure 3:
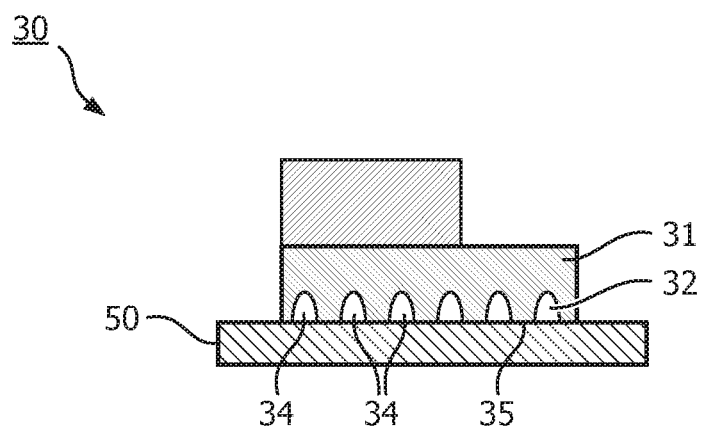
FIG. 3 is a schematic cross-sectional view of a material system with a horizontally stacked configuration of hydrophobic and hydrophilic materials in accordance with still another embodiment of the present invention.

Referring now to FIG. 3, a material system 30 with a horizontally stacked configuration of hydrophobic and hydrophilic materials is illustrated in accordance with one embodiment of the present invention. Material system 30 includes a hydrophobic base material 31 that includes a plurality of holes 34 positioned at an interface 35 of hydrophobic base material 31 with a moist surface, such as skin 50, and a hydrophilic material 32 filling holes 34. As can be seen in FIG. 3, the hydrophilic material 32 may come in contact with skin 50 and, thus, in contact with moisture. Hydrophilic material 32 may accordingly allow for uptake and/or diffusion of moisture away from the contact area of material system 30 with skin 50. Hydrophobic base material 31 may provide the mechanical and dynamical stability of material system 30.

Material system 30 may be, for example, utilized to fabricate an interface material, such as a cushion 41 and a forehead pad 42 of a user interface or patient interface, such as face mask 40, as illustrated in FIG. 4a. The user interface, and, therefore, face mask 40 may be, but is not limited to, a PAP patient interface. Other applications for material system 30 may include, for example, respiratory masks, gas masks, pressurized masks, or diving masks. Skin 50 may be the skin of a person, such as a patient receiving PAP treatment, wearing patient interface 40. Patient interface material 41 may be made in a standard way. However, a mold for patient interface material 41 may be adapted to have small indentations in the patient interface material-face contact 43 area. The mold may be filled with hydrophobic base material 31, such as a hydrophobic silicone material, whereby the indentations of the mold form holes 34. Holes 34 may be filled with a hydrophilic material 32, such as a water free hydrophilic silicone material. If the crosslinking reaction of both silicone materials 31 and 32 is similar and if the crosslinking of hydrophobic base material 31 is not fully complete, hydrophilic material 32 may react with hydrophobic base material 31 and a relatively strong adhesion between the two phases of the materials 31 and 32 may result. If the crosslinking in hydrophobic base material 31 is already complete, such adhesion may be supported by a plasma treatment.

By utilizing material system 30 as in an embodiment of the present invention, an airtight seal may be formed at patient interface-skin contact area 43 allowing for the use of overpressure. The stiffness of patient interface 40 provided by hydrophobic base material 31 may be such that patient interface 40 withstands the overpressure. An improved microclimate at patient interface-skin contact area 43 may be provided by hydrophilic material 32.

By providing material systems 10, 20, and 30 in accordance with various embodiments of the present invention, an improved microclimate at user interface or a patient interface, such as material-face contact area 43 of a patient interface 40 may be created by utilizing various material arrangements, such as layered, mixed, or stacked, of hydrophobic base materials 11, 21, and 31, respectively, and hydrophilic materials 12, 22, and 32, respectively, for the fabrication of mask cushion 41 and forehead pad 42. As a result, a user interface, such as face mask 40, with a sufficient stiffness and a water absorbing and water permeable mask cushion-skin interface 43 may be fabricated in accordance with one embodiment of the present invention. Accordingly, accumulation of moisture at the material skin interface or stratum corneum hyper-hydration of skin 50 may be reduced.

Figure 5:
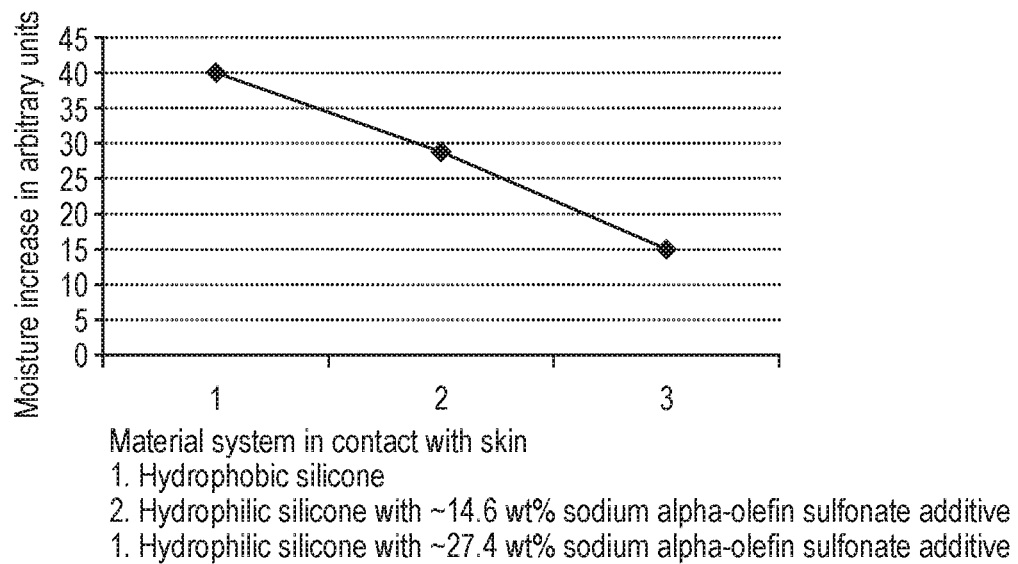
FIG. 5 shows moisture generation by various materials that can be used with the present invention.

The moisture accumulation (given in arbitrary units) if a standard hydrophobic silicone is applied to the skin and a strong reduction of moisture accumulation at the skin is given in FIG. 5 if a hydrophilic silicone is used in contact with the skin.

Figure 6:
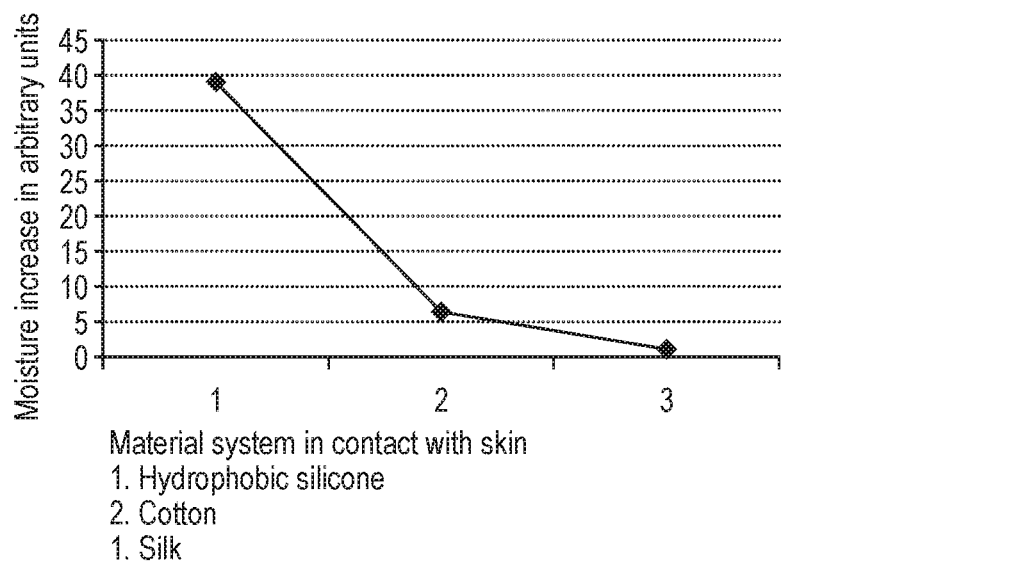
FIG. 6 shows moisture uptake for various materials that can be used with the present invention.

FIG. 6 shows the moisture accumulation at the skin with standard hydrophobic silicones and with textiles such as silk or cotton. A strong reduction of moisture accumulation is obtained if textiles are used in contact with the skin.

The material thus contributes to less moisture accumulation in the skin and increases the tissue tolerance to shear stress and friction and thus to less damage of the skin for example during wearing a patient interface device. The skin contract product thus improves comfort of a patient interface device and supports the reduction of red mark formation, skin irritation, skin damage for example if a patient interface mask is applied to the skin.

In a further embodiment in accordance with the present invention, a novel composition for the preparation of hydrophilic silicone materials suitable for application, for example, in material systems 10, 20, and 30, as described above, is provided. The composition may enable improved mixing and synthesis processes as well as better bulk properties of the obtained hydrophilic material.

The synthesis of a suitable hydrophilic silicone may be described as follows:

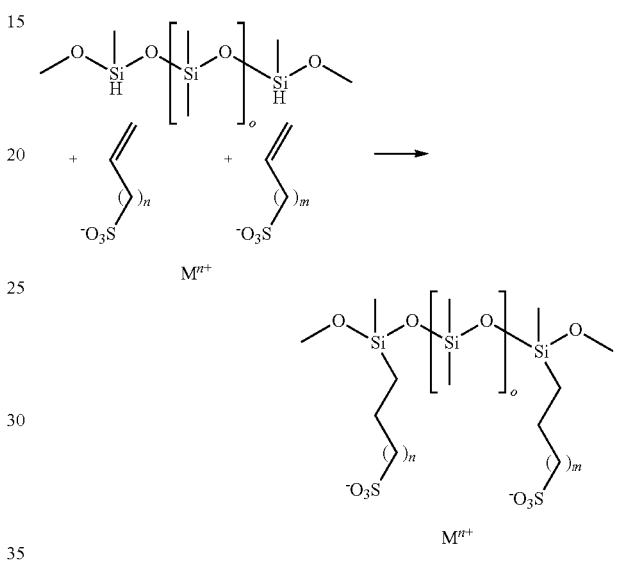

This is the most preferred method as it is combined with a platinum salt catalyzed cross-linking and give medical grade materials. The peroxide or tin salt catalyzed cross-linking can be used for non medical or non biocompatible applications or for parts that do not contact the skin.

A silicone precursor bearing reactive Si—H groups reacts with an alpha-olefin sulfonate, wherein:
  the values for n and m may range from about 1 to 26 or from 3 to 28, preferably range from 10 to 18, and more preferably from 10 to 12 or from 12 to 16,
  the value for o ranges from about 1-10000, or from 5 to 1000, and
  wherein m, n, and o are independent of each other.

The olefin component may be strongly hydrophilic, because it may include a polar, negatively charged head group (—O3S) and a cation (Mn+) for charge balance. The mixing of the hydrophilic olefin component with the hydrophobic silicone precursor may be hampered by the difference in hydrophilicity. It may be particularly different to suspend the ion pair composed of the anionic head group and the cationic counterion in the hydrophobic matrix of the silicone precursor.

Adding a crown ether as a solubility or mixing mediator may be highly effective and may allow for a simple, rapid, and highly reproducible synthesis of the desired hydrophilic silicone material. The choice of the most suitable crown ether may depend on the counter cation used. For instance, the most efficient solubility mediator for dissolving sodium ions in hydrophobic media is the 15-crown-5 ether, whereas the most suitable solubility mediator for dissolving potassium ions in hydrophobic media is the 18-crown-6 crown ether. The stabilization of metal ions in hydrophobic media by crown ethers, derivatives thereof, and related molecules, is well known in the art and has been described for instance in the following publications, the content of which is incorporated herein by reference:

H. J. Schneider et al., Chemical Society Reviews, 2008, 37, 263-277;

Barannikov, Russian Journal of Coordination Chemistry, 2002, 28, 153-162; and

J. W. Steed, Coordination Chemistry Reviews, 2001, 215, 171-221; and in references therein.

In an exemplary embodiment in accordance with the present invention, mixing a commercial silicone precursor material with a sodium alpha-olefin sulfonate may be facilitated by the addition of a crown ether mixing mediator. Sodium alpha-olefin sulfonates, such as sodium C12-14 olefin sulfonate, sodium C14-16 olefin sulfonate, sodium C14-18 olefin sulfonate, or sodium C16-18 olefin sulfonate, are mixtures of long chain sulfonate salts prepared by the sulfonation of alpha olefins. The numbers indicate the average length of the carbon chains of the alpha olefins. Other ligating compounds that may be suitable to form an inclusion complex with the chosen counter ion may be used as an alternative to crown ethers. An example of such compounds are calix[4]arenes as described in B. S. Creaven et al., Coordination Chemistry Reviews, 2009, 253, pp. 893-962, the content of which is incorporated herein by reference.

The water-absorbing rubbery or elastomeric polymer material for use in the user interface device, or wound dressing, with high water-uptake capacity may be in the form of a fiber or fibrous material. Manufacture of polymer fibers, in particular silicone fibers such as used as fillers in polyester pillows, in particular hollow silicone fibers with a linear mass density from 1.5 to 25 deniers, are well known to the skilled person.

The water-absorbing rubbery or elastomeric polymer material for use in the user interface device, or wound dressing, with high water-uptake capacity of the present invention may also be in the form of a polymer foam, in particular a silicone-based foam, in which case a suitable silicone-based foaming composition is required. This foaming composition may be defined for instance as comprising:

one or more hydrophobic organic monomers selected from the group consisting of dialkylsiloxanes and diarylsiloxanes, or a silicone precursor, a monomer or polymer with one or more hydrophilic side groups, one or more hydroxylated components, from 1 to 250 ppm of a platinum catalyst, and optionally a foam density-reducing amino component.

Exemplary details of such foaming compositions are provided below.

A hydroxyl source is necessary to properly blow the foamable composition and may be in the form of one or more hydroxylated components. The source of hydroxyl may be selected from the group consisting of water, organic alcohols, silanols and mixtures thereof. Suitable silanols include any hydroxylated organosiloxane having an average of 1 to 2.5 silicon-bonded hydroxyl radicals per molecule. The silanols may be monomers, homopolymers, copolymers or mixtures thereof. Examples of suitable silanols include, but are not limited to, hydroxyl end-capped polydimethylsiloxane, hydroxyl end-capped dimethylsiloxane/phenylmethyl-siloxane copolymers, hydroxyl end-capped polymethyl-3,3,3-trifluoropropylsiloxane and diphenylmethylsilanol.

Organic alcohols suitable for use in the foaming compositions herein may be mono-alcohols or polyols, preferably having from 1 to 12 carbon atoms. Suitable organic alcohols include, but are not limited to, ethanol, propanol, butanol, lauryl alcohol, octyl alcohol, ethylene glycol, and benzyl alcohol. The hydroxyl source may react with hydrogen of the hydrophobic siloxane or silicone precursor to produce hydrogen gas. Water will react with hydrogen of the hydrophobic siloxane or silicone precursor to produce a hydroxyl function which can further react to produce additional gas and a cross-link site. Thus, where water is the hydroxyl source, additional gas will be generated as a benefit, but gassing after cure may occur. Silanol, due to good solubility in the composition, produces gas immediately but may lead to problems of premature gelation. Organic alcohols do not as easily react with the hydrogen function and thus are generally used in combination with silanol or water. Depending on the hydroxyl source used, there should preferably be from 0.02 to 5 hydroxyl groups from the hydroxyl source for each silicone-bonded hydrogen atom in the hydrophobic siloxane or silicone precursor. Alternatively the hydroxylated component(s) should constitute not more than 2% by weight of the foamable composition of the present invention.

Suitable platinum catalysts are preferably soluble in the other ingredients of the foaming composition of the present invention. Although this is not a limiting feature of the present invention, they can be selected from the group of compounds having the formulae (PtCl2.Olefin)2 and H(PtCl3.Olefin), as described in U.S. Pat. No. 3,159,601. The olefin shown in these formulae is preferably an aliphatic alkene having from 2 to 8 carbon atoms, a cycloalkene having from 5 to 7 carbon atoms, or an alkenylaryl compound such as styrene. Specific suitable olefins include, but are not limited to, ethylene, propylene, butene, octene, cyclopentene, cyclohexene, and cycloheptene, A further suitable platinum catalyst for the foaming composition of the present invention is the platinum chloride cyclopropane complex (PtCl2C3H6)2 described in U.S. Pat. No. 3,159,662, or a complex formed from chloroplatinic acid with up to 2 moles per gram of platinum of a ligand selected from the group consisting of alcohols, ethers, aldehydes and mixtures thereof as described in U.S. Pat. No. 3,220,972.

Another suitable platinum catalyst (see U.S. Pat. No. 3,775,452) may be formed by reacting chloroplatinic acid containing 4 moles of water of hydration with tetramethyl-tetravinylcyclosiloxane in the presence of sodium bicarbonate in an ethanol solution.

Platinum catalysts such as illustrated above may be deposited on carriers such as silica gel or powdered charcoal.

An amino compound optionally suitable and effective to lower silicone foam density has the formula NR3 wherein each R is independently selected from the group consisting of hydrogen, hydroxyl, C1-18 alkyl, C3-10 cycloalkyl, aryl (e.g. phenyl), and silyl, provided that at most one R may be hydroxy and provided that not all three R are hydrogen. Suitable amino compounds include, but are not limited to, hydroxylamines (e.g. diethyl hydroxyl amine), primary, secondary and tertiary amines, and silylamines, for example tetramethylpiperidine, piperidine, N-methylmorpholine, N,N-dimethyl-ethylenediamine, N-methylipiperidine, N-hexylamine, tributylamine, dibutylamine, cyclohexylamine, di-n-hexylamine, triethylamine, benzylamine, dipropylamine, N-ethyl-phenylamine, tetramethyl-guanidine, hexamethyl-disilazane and N-methylmorpholine. Preferably the amino compound should be soluble in the foamable composition for use in the present invention.

Hydrophobic organic monomers suitable for the foaming compositions for use in the invention include, but are not limited to, polysiloxanes having not less than 5 alkylhydrogensiloxane units per molecule, polysiloxanes having not less than two silicon-bonded hydroxyl groups per molecule, fluorinated polyorganosiloxanes. Monomers or polymers with hydrophilic side groups suitable for the foaming compositions of the invention are as described previously with respect to embodiments of hydrophilic silicone materials.

Preferably, the foaming composition for use in the invention is provided in the form of two or more parts for admixture just prior to forming said composition, and each of said parts preferably has a similar viscosity as the other one at 25°.

Reactions of components of the foaming compositions to generate hydrogen gas and to cure the mass through chain extension and crosslinking within the desired time span are dependent on presence of appropriate proportions of these components, especially the alkylhydrogen polysiloxane. Preferably this polysiloxane should have from 0.5% to 2.5% by weight of silicon-bonded hydrogen atoms.

These components of the foaming compositions are preferably liquids with appropriate functionality and chain length to achieve the target viscosity required for the composition, the amount of hydrogen evolution and the degree of chain extension and crosslinking required during curing of the composition. Suitable polysiloxanes having silicon-bonded hydroxyl groups are preferably silanol terminated polydiorganosiloxanes.

One may optionally include, in the foaming hydrophilic silicone composition for use in the invention, appropriate amounts of higher functional materials as crosslinking agents. Suitable crosslinking agents include materials having three or more functional, e.g. hydroxyl, groups per molecule. Preferred crosslinking agents include an alkoxysilane and/or a condensation product thereof capable of combining with three or more hydroxy polysiloxane molecules with release of the corresponding alcohol, e.g. methyl trimethoxysilane, n-propylortho-silicate or ethyl polysilicate.

The foaming compositions for use in the present invention may also include up to 10 percent, based on the weight of the hydrophobic siloxane, of $GSiO_{3/2}$ units wherein G is a residue obtained by removing the hydrogen atom from a hydroxyl group of a linear organic polymer selected from the group consisting of homopolymers of ethylenically unsaturated alcohols, copolymers of these alcohols with ethylenically unsaturated hydrocarbons, polyethers and polyoxyalkylene glycols, wherein said organic polymer contains an average of at least one terminal hydroxyl group per molecule, as described in European Patent No. 179.598.

Within the above definitions of various embodiments of the foaming compositions for use in the present invention, one may obtain rubbery or elastomeric silicone materials being in the form of a foam with a foam density from 60 to 300 kg/m3. For instance, high density foams from 150 to 300 kg/m3, or low density foams from 60 to 150 kg/m3.

The following examples are purely illustrative of specific embodiments and should not be understood or construed as limiting the scope of the invention.

Example 1

The commercial silicone elastomer Elastosil LR 3004/40 (Wacker Silicones, Germany) was used as silicone precursor material. The silicone precursor material is a two component system that has to be mixed in a 1:1 ratio of the two components A and B. The A component consists of a pre-polymer bearing reactive vinyl groups and a platinum catalyst. The B component consists of a pre-polymer bearing reactive vinyl groups and a pre-polymer bearing Si—H groups. The silicone composition was comprised of 90% of the commercial silicone precursor and 10% of a commercial sodium alpha-olefin sulfonate.

The commercial sodium alpha-olefin sulfonate was first mixed with the A component of the silicone precursor material. This mixing process is generally energy-demanding as the two components are viscous and do not mix well. An example of the energy/shear that is needed is given in the international patent application WO2010/095105, where the incorporation of the surfactant in Elastosil LR3003/60 is mentioned. Heating to 120° C. was needed to incorporate the surfactant. The used Elastosil 3004/40 was found to be even more viscous than Elastosil LR3003/60.

To facilitate mixing of the commercial sodium alpha-olefin sulfonate with the silicone precursor A component, a crown ether (15-crown-5) was used (10% w/w with respect to the total amount of components A+B) as a mixing mediator. After addition of the crown ether, mixing was found to be straight forward and easily accomplished at room temperature.

More specifically, commercial sodium alpha-olefin sulfonate (2 g) was mixed with 15-crown-5 (2 g) and silicone precursor A component (10 g). Mixing was performed at room temperature (SpeedMixer™ DAC 150 FVZ-K, Hauschild, Germany, 2×2 min, 3300 rpm). Then silicone precursor B component (11.4 g) was added and the obtained composition was mixed again (SpeedMixer™ DAC 150 FVZ-K, Hauschild, Germany, 2×2 min, 3300 rpm). The new silicone composition was thus comprised of 84% wt of the commercial silicone precursor material, 8% wt of a commercial sodium alpha-olefin sulfonate, and 8% wt of the mixing mediator 15-crown-5.

Material samples were prepared by casting the above mixture onto the surface of a glass substrate and curing (30 min, 130° C.) under reduced pressure (<10 mbar). After curing, the water uptake of the new silicone material (sample A) was compared with that of two other materials: a material sample that was made with 20% wt of the sodium alpha-olefin sulfonate without crown ether (sample B) and a material sample that was made of the commercial silicone elastomer Elastosil 3004/40 according to the instructions of the manufacturer (sample C). After immersion of all three samples in demineralized water for 5 days, the Elastosil 3004/40 (sample C) had taken up 0.3% wt of water, the new silicone material comprising the sodium alpha-olefin sulfonate and the crown ether mixing mediator (sample A) had taken up 43% wt of water, whereas the sample B comprising only the sodium alpha-olefin sulfonate but no 15-crown-5 mixing mediator, had taken up 40% wt of water.

Figure 7:
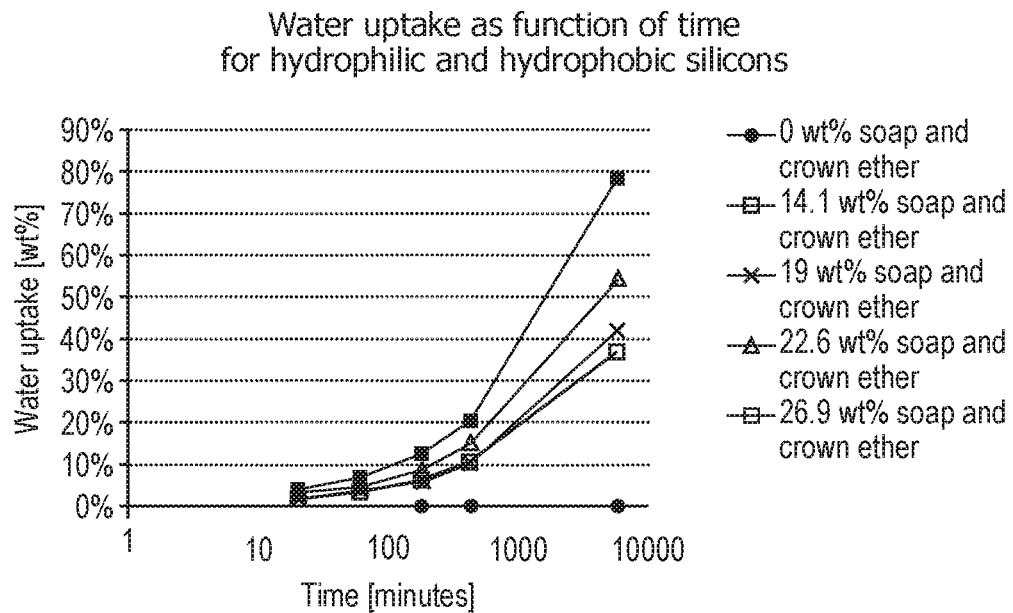
FIGS. 7 and 8 show the water uptake of different hydrophilic silicone rubber materials (wherein the term "soap" is used as an abbreviation to designate sodium sulfonate groups) as a function of time, in comparison with a hydrophobic silicone rubber material without alkylsulfonate groups.

Water uptake (weight %) as a function of time of different amounts of sodium C12-14 alkenyl sulfonate with equal amounts of 15-crown-5 in Elastosil LR3004/40 along the route described herein are shown in FIG. 7.

As can be seen, a composition for the preparation of hydrophilic silicone materials is disclosed in accordance to a one embodiment of the present invention, that enables improved mixing and synthesis processes leading to improved hydrophilic bulk properties of the obtained hydrophilic silicone. The obtained hydrophilic silicone in accordance with one embodiment of the present invention may be utilized in various elements of a user or patient interface, such as cushions 41 and forehead pads 42 of patient interface 40, which may be, for example, a mask for positive air pressure therapy of obstructive sleep apnea, in accordance with another embodiment of the present invention. The hydrophilic silicone including a silicone precursor material, a sodium alpha-olefin sulfonate, and a crown ether mixing mediator may allow for an effective removal of moisture from the patient interface-skin contact area by either uptake of the moisture in the hydrophilic silicone or by diffusion of the moisture through the hydrophilic silicone away from a user interface, such as the face mask-skin contact region. Thus, an improved microclimate may be created at the patient interface-skin contact area, which may result in reduced moisture accumulation, reduced skin irritation, and reduced skin damage and reduced red mark formation.

In the following examples 2-5, the amount of commercial sodium C12-14 alkenyl sulfonate added to the amount of silicone precursors A+B is given in percentage and calculated along weight sodium C12-14 alkenyl sulfonate/weight silicone A+B*100. The values for the percentage silicone precursor A+B given in the examples 2-5 are the values for 100%−amount sodium C12-14 alkenyl sulfonate %.

Example 2

The commercial silicone elastomer Elastosil LR 3004/40 (Wacker Silicones, Germany) was used as silicone precursor material. The silicone precursor material is a two component system that was mixed in a 1:1 weight ratio of two components A and B. The A component consists of a silicone pre-polymer bearing reactive vinyl groups and a platinum catalyst. The B component consists of a silicone pre-polymer bearing reactive vinyl groups and a pre-polymer bearing Si—H groups.

The sodium alpha-olefin sulfonate $RCH=CH(CH_2)_nSO_3Na$ (n=12-14) commercially available from The Chemistry Store.com (Cayce, S.C., United States) with an average particle size above 400 μm was first mixed with the A component of the silicone precursor material. This mixing process is generally energy-demanding as the two components are viscous and do not mix well. Heating to 120° C. may therefore be needed.

To facilitate mixing of the commercial sodium alpha-olefin sulfonate with the silicone precursor A component, a crown ether (15-crown-5) acetone mixture was used as a mixing mediator. After addition of the crown ether and acetone mixing was found to be straight forward and easily accomplished at room temperature.

More specifically, the commercial sodium alpha-olefin sulfonate (12 g) was mixed in a first step with 15-crown-5 (7 g) and 7 g acetone. After this the silicone precursor A component (19 g) was added. Mixing was performed at room temperature (Speed Mixer™ DAC 150 FVZ-K, Hauschild, Germany, twice 2 minutes, 3300 rpm). The crown ether and acetone were removed in vacuum at 0.05 mbar, 90° C. Then silicone precursor B component (26.1 g) was added and the obtained composition was mixed again (same mixer, twice 2 minutes, 3300 rpm). The resulting silicone composition was thus comprised of 73.4% by weight of the commercial silicone precursor material, and 26.6% by weight of the commercial sodium alpha-olefin sulfonate.

Material samples were prepared by casting the above mixture onto the surface of a glass substrate and curing (30 minutes, 130° C.) under N2 atmosphere.

Example 3

In a further example the commercial silicone elastomer Elastosil LR 3004/40 (Wacker Silicones, Germany) was used as silicone precursor material. The silicone precursor material is a two component system that was mixed in a 1:1 weight ratio of two components A and B. The A component consists of a silicone pre-polymer bearing reactive vinyl groups and a platinum catalyst. The B component consists of a silicone pre-polymer bearing reactive vinyl groups and a pre-polymer bearing Si—H groups.

A commercial sodium alpha-olefin sulfonate $RCH=CH(CH_2)_nSO_3Na$ (n=12-14) from Stepan Company was used. This very fine powder with particle sizes <400 um was mixed with the A component of the silicone precursor material by speed mixing. More specifically, commercial sodium alpha-olefin sulfonate (12 g) was mixed with silicone precursor A component (19 g). Then silicone precursor B component (26.1 g) was added and the obtained composition was mixed. The resulting silicone composition was thus comprised of 73.4% by weight of the commercial silicone precursor material, and 26.6% by weight of a commercial sodium alpha-olefin sulfonate.

Patient interface devices were prepared by pressure molding at 130° C. (see FIG. 4b for an example of the device).

Example 4

In a further example the commercial silicone elastomer Elastosil LR 3004/40 (Wacker Silicones, Germany) was used as silicone precursor material. The silicone precursor material is a two component system that was mixed in a 1:1 weight ratio of two components A and B. The A component consists of a silicone pre-polymer bearing reactive vinyl groups and a platinum catalyst. The B component consists of a silicone pre-polymer bearing reactive vinyl groups and a pre-polymer bearing Si—H groups.

A commercial sodium alpha-olefin sulfonate $RCH=CH(CH_2)_nSO_3Na$ (n=12-14) from Stepan Company was used. This very fine powder (12 g) was mixed with 7 g ethanol. Then 19 g of the A component of the silicone precursor material added and mixing was carried out with a speed mixer. After mixing the ethanol was removed under vacuum at 60° C. Then silicone precursor B component (26.1 g) was added and the obtained composition was mixed. The resulting silicone composition was thus comprised of 73.4% by weight of the commercial silicone precursor material, and 26.6% by weight of a commercial sodium alpha-olefin sulfonate.

Patient interface devices were prepared by pressure molding at 130° C. (see FIG. 4b for an example of the device).

Example 5

In a further example the commercial silicone elastomer Elastosil LR 3004/40 (Wacker Silicones, Germany) was used as silicone precursor material. The silicone precursor material is a two component system that was mixed in a 1:1 weight ratio of two components A and B. The A component consists of a silicone pre-polymer bearing reactive vinyl groups and a platinum catalyst. The B component consists of a silicone pre-polymer bearing reactive vinyl groups and a pre-polymer bearing Si—H groups.

A commercial sodium alpha-olefin sulfonate $RCH=CH(CH_2)_nSO_3Na$ (n=12-14) from Stepan Company was used. This very fine powder 12 g was mixed with 7 g of an ethanol water mixture (50/50% by volume). Then 19 g of the A component of the silicone precursor material added and mixing was carried out with a speed mixer. After mixing the ethanol was removed under vacuum at 90° C. Then silicone precursor B component (26.1 g) was added and the obtained composition was mixed. The resulting silicone composition was thus comprised of 73.4% by weight of the commercial silicone precursor material, and 26.6% by weight of a commercial sodium alpha-olefin sulfonate.

Patient interface devices were prepared by pressure molding at 130° C. (see FIG. 4b of the device).

Figure 8:
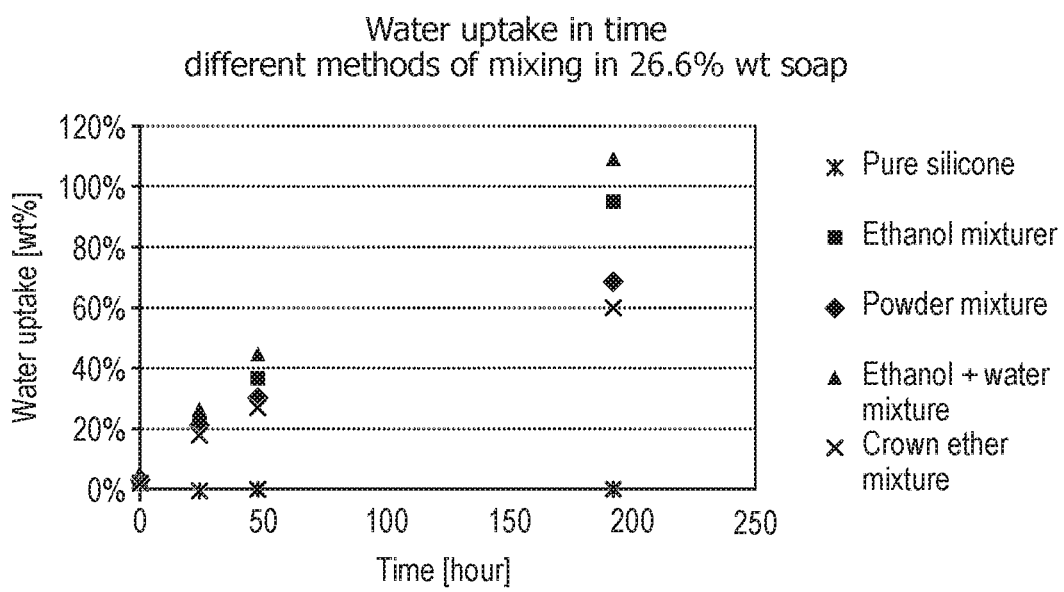

Water uptake (weight %) as a function of time of different mixing methods of sodium C12-14 alkenyl sulfonate with Elastosil LR3004/40 along the above route described in examples 2-5 is given in FIG. 8.

Example 6

In a further example in a 2.5 litre jacketed glass reactor a mixture of 55 grams butylmethacrylate (BMA) (99%+) and 2200 grams water of a conductivity of 18.2 MΩ·cm and a 0.6 g commercial sodium alpha-olefin sulfonate RCH═CH(CH2)nSO3Na (n=12-14) from Stepan Company are mixed and degassed under nitrogen while stirring at 500 rpm (using a double bladed stirrer). In order to reduce the chain length of the polymer, by controlling the micelle size of the BMA droplets in water, from 1 to 2% by weight of surfactant (e.g. sodium alpha-olefin sulfonate) is added to the monomer mixture. Then the reactor is put under nitrogen and the mixture is heated to 80° C. After addition of the initiator solution (for instance 1.6 g ammonium persulfate 98% in 50 g of water of a conductivity of 18.2 MΩ·cm) at 80° C., the stirring speed is reduced to 350 rpm. Polymerisation is carried out for at least 3 hours.

Example 7

In this example the commercial silicone elastomer Elastosil LR 3003/5 (commercially available from Wacker Silicones, Germany) was used as the silicone precursor material. The silicone precursor material is a two component system that was normally mixed in a 1:1 weight ratio of two components A and B. The A component consists of a silicone pre-polymer bearing reactive vinyl groups and a platinum catalyst. The B component consists of a silicone pre-polymer bearing reactive vinyl groups and a pre-polymer bearing Si—H groups. A commercial sodium alpha-olefin sulfonate RCH═CH(CH2)nSO3Na (n=12-14) from Stepan Company (Northfield, Ill., United States) was used. 12 g of this very fine powder (particle sizes below 400 μm) was mixed with 7 g of an ethanol water mixture (50/50% by volume). Then 19 g of the A component of the silicone precursor material was added and mixed with a speed mixer. After mixing the ethanol and water were removed under vacuum at 60° C. until a small amount (±0.5 gram) of water was still present. Then silicone precursor B component (24.7 g) was added and the obtained composition was mixed. The commercial sodium alpha-olefin sulfonate added to the silicone precursors A+B, is thus amounting to 27.5 weight % of silicone precursor (A+B) weight ((weight sodium alpha-olefin sulfonate/weight silicone A+B)*100). The mixing ratio of this system for component A to B was 1 to 1.3. Material samples were prepared by pressure molding at 130° C. for 10 to 15 minutes at 711 psi.

While the invention has been described by reference to various specific embodiments, it should be understood that numerous changes may be made within the spirit and scope of the inventive concepts described. Accordingly, it is intended that the invention not be limited to the described embodiments, but will have full scope defined by the language of the following claims.

The invention claimed is:

1. A polymerizable composition comprising:
   (a) a hydrophobic organic monomer or pre-polymer,
   (b) a hydrophilic monomer being an alkenyl sulfonate having 3 to 28 carbon atoms in association with a cation, and
   (c) a ligating compound for said hydrophilic monomer (b) in an amount sufficient to dissolve the cation and achieve solubility or miscibility of said hydrophilic monomer (b) in said hydrophobic organic monomer or pre-polymer (a), wherein said composition yields a rubbery or elastomeric polymer material taking up more than 5% by weight of water and up to 500% by weight of water after immersion in demineralized water at room temperature for a sufficient time to reach saturation.

2. A polymerizable composition according to claim 1, wherein said hydrophilic monomer (b) reacts or associates with said ligating compound (c) and wherein, after reaction or association with said ligating compound (c), is able to react with said hydrophobic organic monomer or pre-polymer (a) under liquid phase polymerization conditions wherein said hydrophilic monomer (b) is incorporated into the polymer sequence resulting from liquid phase polymerization of said hydrophobic organic monomer or pre-polymer (a).

3. A polymerizable composition according to claim 1, wherein said ligating compound is selected from the group consisting of a crown ether, a cryptand and a calixarene.

\* \* \* \* \*